US009670245B2

(12) United States Patent
Ren et al.

(10) Patent No.: US 9,670,245 B2
(45) Date of Patent: Jun. 6, 2017

(54) GINSENOSIDE C-K POLYMORPHIC COMPOUNDS AND METHOD FOR PREPARING SAME

(71) Applicant: Zhejiang Hisun Pharmaceutical Co., Ltd., Zhejiang (CN)

(72) Inventors: Guobin Ren, Shanghai (CN); Changliang Dai, Zhejiang (CN); Jinyao Chen, Shanghai (CN); Feng Chen, Zhejiang (CN); Minghui Qi, Shanghai (CN); Wenming Zhu, Zhejiang (CN); Minghuang Hong, Shanghai (CN); Hua Bai, Zhejiang (CN)

(73) Assignee: Zhejiang Hisun Pharmaceutical Co., Ltd., Zhejiang (CN)

( * ) Notice: Subject to any disclaimer, the term of this patent is extended or adjusted under 35 U.S.C. 154(b) by 150 days.

(21) Appl. No.: 14/389,357

(22) PCT Filed: Apr. 1, 2013

(86) PCT No.: PCT/CN2013/073560
§ 371 (c)(1),
(2) Date: Sep. 29, 2014

(87) PCT Pub. No.: WO2013/149570
PCT Pub. Date: Oct. 10, 2013

(65) Prior Publication Data
US 2015/0065699 A1 Mar. 5, 2015

(30) Foreign Application Priority Data
Apr. 1, 2012 (CN) .......................... 2012 1 0093275

(51) Int. Cl.
C07J 17/00 (2006.01)
(52) U.S. Cl.
CPC ............. *C07J 17/00* (2013.01); *C07J 17/005* (2013.01); *C07B 2200/13* (2013.01)
(58) Field of Classification Search
CPC ...... C07J 17/00; C07J 17/005; C07B 2200/13
USPC .......................................................... 536/5
See application file for complete search history.

(56) References Cited

U.S. PATENT DOCUMENTS

2002/0048610 A1  4/2002  Cima et al.

FOREIGN PATENT DOCUMENTS

| CN | 1417345 A | 5/2003 |
|---|---|---|
| CN | 1465694 A | 1/2004 |
| CN | 1570133 A | 1/2005 |
| CN | 101139562 A | 3/2008 |
| CN | 101921304 A | 12/2010 |
| CN | 102251009 A | 11/2011 |
| CN | 101921304 A | 12/2012 |
| CN | 103087138 A | 5/2013 |
| JP | 2003519698 A | 6/2003 |

OTHER PUBLICATIONS

Zhou et al, Chemistry & Biodiversity, 2009, 6, 38-388.*
Li et al, Cryst. Res. Tech., 2012, 47(4), 377-384.*
Japanese Office Action, dated Nov. 24, 2015, from corresponding Japanese Application No. 2015-502083.
Cui-Cui et al.: "Extraction of ginsenoside Compound-K," Journal of Dalian Polytechnic University 2009, v.28, pp. 87-89.
Kawaguchi et al.: "Drug and crystal polymorphism," Journal of human environmental engineering 2002, v.4, pp. 310-317.
"Setting new drugs on the specifications and test methods," Pharmaceutical trial departure No. 568, 2001, Pharm Stage 2007, vol. 6, No. 10, p. 48-53.
"Crystallization of Polymorphs and Pseudo-polymorphs and Its Control," Pharm Stage 2007, vol. 6, No. 10, p. 48-53.
"API from screening and selection in drug discovery stage," Pharm Stage 2007, vol. 6, No. 10, p. 20-25.
Yamano: "Approach to Crystal Polymorph in Process Research of New Drug," Journal of Synthetic Organic Chemistry, Japan 2007,vol. 65, No. 9,p. 907-913.
Bryn et al.: "Pharmaceutical Solids: A Strategic Approach to Regulatory Considerations," Pharmaceutical Research 1995, v.12, pp. 945-954.
International Search Report dated Jul. 11, 2013from corresponding International Application No. PCT/CN2013/073560.
International Search Report dated Jul. 11, 2013 from potentially related International Application No. PCT/CN2013/073562.
Zhou, W., *Studies on the preparation, crystal structure and bioactivity of ginsenoside compound K*, Journal of Asian Natural Products Research, vol. 8, No. 6, Sep. 2006, 519-527.
Zhou, W, et al., *X-Ray Structure Investigation of (20S)-20-O-β-D-glucopyranosyl-protopanaxadiol and antitumor effect on Lewis lung carcinoma in vivo*. Chemistry & Biodiversity, 2009, vol. 6, pp. 380-388.
Zhou, W, *Studies on the preparation, crustal structure and bioactivity of ginsenoside compound K*, Chinese Doctoral Dissertations Full-text Database (Medicine and Health Sciences). No. 3, pp. 51-52, Feb. 10, 2009.
Partial European Search Report, dated Oct. 13, 2015, from corresponding or related European Patent Application No. 13773118.8.
Runyan Li et al: "Isolation, characterization and phase transformation of new ginsenoside compound k hydrate and methanol solvates," (2012) Cryst. Res. Technol.; vol. 4; pp. 377-384.
Wei Zhou et al: "X-ray Structure Investigation of 20-O-B-D-glucopyranosyl-20(S)-protopanaxadiol," (2009) J Chem Crystallogr; vol. 39; pp. 99-103.
Zhou, Wei et al: "Method for purifying ginsenoside compound-k with macroporous resin" (2010) XP-002743475.

(Continued)

*Primary Examiner* — Ganapathy Krishnan
(74) *Attorney, Agent, or Firm* — Wolf, Greenfield & Sacks, P.C.

(57) ABSTRACT

Provided are several types of ginsenoside polymorphic substances and a method for preparing same. In particular, new crystal form A, crystal form B, crystal form C, crystal form E, crystal form F, crystal form I, crystal form K, crystal form L, crystal form M, crystal form N, and crystal form O are involved.

8 Claims, 18 Drawing Sheets

(56) References Cited

OTHER PUBLICATIONS

Ji-Eun Shin et al: "Cytotoxicity of Compound K (IH-901) and Ginsenoside $R_{h2}$, Main Biotransformants of Ginseng Saponins by Bifidobacteria, against Some Tumor Cells," (2003) J. Ginseng Res.; vol. 27; pp. 129-134.
Im Kwang Sik et al: "A modified alkaline hydrolysis of total ginsenosides yielding genuine aglycons and prosapogenols," (1995) Arch. Pharm. Res.; vol. 18; pp. 454-457.
Gu Huike et al: "Molecular modeling of crystal morphology of ginsenoside compound K solvates and its crystal habit modification by solvent molecules," (2013) Journal of Crystal Growth; vol. 373; pp. 146-150.
Runyan Li et al: "Correlation of Solubility and Prediction of the Mixing Properties of Ginsenoside Compound K in Various Solvents," (2012) Industrial & Engineering Chemistry Research; vol. 51; pp. 8141-8148.

\* cited by examiner

GINSENOSIDE C-K POLYMORPHIC COMPOUNDS AND METHOD FOR PREPARING SAME

CROSS REFERENCE TO RELATED APPLICATIONS

This application is the national phase of International Application No. PCT/CN2013/073560, filed on Apr. 1, 2013, which claims the benefit of priority to Chinese Patent Application No. 201210093275.5, filed with the Chinese State Intellectual Property Office on Apr. 1, 2012, which applications are incorporated herein by reference to the maximum extend allowable by law.

FIELD OF THE INVENTION

The present invention relates to the pharmaceutical field, and more particularly, the present invention relates to polymorphic forms of ginsenoside C-K and the method for preparing the same.

BACKGROUND OF THE INVENTION insenosides are primary active ingredients of ginseng, in which ginsenoside C-K belongs to a diol-type ginsenoside, and is not present in natural ginseng. Ginsenoside C-K is the major degradation product of other diol-type ginsenosides in human intestinal tract, which is indeed the entity that is absorbed and effects in the human body. Ginsenoside C-K not only has favorable activities in the aspects including anti-tumor, anti-inflammation, anti-allergy, liver protection and the like, but also plays a good role in regulation of both nervous system and immune system.

At present, reference 1 (Studies on the preparation, crystal structure and bioactivity of ginsenoside compound K, *Journal of Asian Natural Products Research*, 2006, 8(6), 519-527) has reported a crystal form of ginsenoside C-K, which is designated as crystal form G. It has been reported that the crystal form is a dihydrate of ginsenoside C-K, which belongs to the monoclinic system and has the following cell parameters: a=15.992(3) Å, b=11.960(19) Å, c=20.127(3) Å, α=90°, β=101.85°, γ=90°, V=3767.5(11)Å$^3$, and Z=4, in which the solvent system used consists of acetonitrile and water.

Generally, for an active pharmaceutical ingredient, the bioavailability may vary due to different crystal forms. Furthermore, physicochemical properties, including stability, flowability and compressibility may also be different, which will have certain influence on its applications. The various crystal forms of ginseno side C-K provided in the present invention have certain difference from each other in their physicochemical properties.

SUMMARY OF THE INVENTION

Several novel crystal forms of ginsenoside C-K are provided in the present invention, including crystal form A, crystal form B, crystal form C, crystal form E, crystal form F, crystal form I, crystal form K, crystal form L, crystal form M, crystal form N, and crystal form O, and the preparation methods for some of the crystal forms are also provided.

In one aspect of the present invention, a crystal form A of ginsenoside C-K is provided, in which there are diffraction peaks at 2θ values (°) of about 5.44, 7.06, 8.94, 11.61, 13.70, 14.43, 15.81, 17.22, 17.84, 18.71 and 19.01 in the XRPD pattern, and preferably, these peaks are major diffraction peaks, in which the error range of 2θ value is ±0.2.

In further embodiments, the crystal form A also has diffraction peaks at 2θ values (o) of about 9.51, 12.28, 16.14, 20.90, 21.90, 25.68, and 27.71, and preferably, these peaks are minor diffraction peaks, in which the error range of 2θ value is ±0.2.

In further embodiments, the crystal form A of ginsenoside C-K has diffraction peaks of the XRPD pattern substantially as shown in FIG. 1.

The specific data of the XRPD pattern are listed in the table below:

TABLE 1

The data of XRPD diffraction angles of the crystal form A of ginsenoside C-K

| No. | 2θ | I % |
| --- | --- | --- |
| 1 | 5.44 | 10.5 |
| 2 | 7.06 | 10 |
| 3 | 8.94 | 100 |
| 4 | 9.51 | 7.8 |
| 5 | 11.61 | 9.6 |
| 6 | 12.28 | 6.8 |
| 7 | 13.70 | 29.7 |
| 8 | 14.43 | 41.4 |
| 9 | 15.43 | 16.4 |
| 10 | 15.81 | 26.6 |
| 11 | 16.14 | 12.8 |
| 12 | 17.22 | 31.6 |
| 13 | 17.84 | 16.5 |
| 14 | 18.71 | 29.4 |
| 15 | 19.01 | 16.4 |
| 16 | 20.90 | 6 |
| 17 | 21.90 | 7.3 |
| 18 | 25.68 | 6.7 |
| 19 | 27.71 | 7.4 |

In further embodiments, the crystal form A of ginsenoside C-K has an endothermic peak of around 117±5° C. in the DSC pattern.

In another aspect of the present invention, a method for preparing the crystal form A of ginsenoside C-K is provided, comprising: (1) dissolving ginsenoside C-K in 1-methyl-2-pyrrolidone or a mixed solvent consisting of 1-methyl-2-pyrrolidone and acetone; (2) removing the solvent slowly by evaporation; (3) drying the resultant solid under vacuum to obtain the crystal form A of ginsenoside C-K.

In another aspect of the present invention, another method for preparing the crystal form A of ginsenoside C-K is provided, comprising: (1) dissolving ginsenoside C-K in 1-methyl-2-pyrrolidone; (2) adding an anti-solvent dropwise; (3) after stirring for a while, filtering the resultant suspension, and drying the filter cake under vacuum to obtain the crystal form A of ginsenoside C-K. The anti-solvent is selected from the group consisting of isopropyl ether, water and nitromethane.

In another aspect of the present invention, a crystal form B of ginsenoside C-K is provided, characterized in that there are diffraction peaks at 2θ values (°) of about 5.31, 9.73, 9.89, 10.70, 11.25, 13.83, 16.14, 16.85, and 18.69 in the XRPD pattern, and preferably, these peaks are major diffraction peaks, in which the error range of 2θ value is ±0.2.

In further embodiments, the crystal form B also has diffraction peaks at 2θ values (o) of about 14.92, 15.16, 18.17, 20.04, 20.41, 29.43, and 34.56, and preferably, these peaks are minor diffraction peaks, in which the error range of 2θ value is ±0.2.

In further embodiments, the crystal form B of ginsenoside C-K has diffraction peaks of the XRPD pattern substantially as shown in FIG. 3.

The specific data of the XRPD pattern are listed in the table below:

TABLE 2

The data of XRPD diffraction angles of the crystal form B of ginsenoside C-K

| No. | 2θ | I % |
| --- | --- | --- |
| 1 | 5.31 | 28.4 |
| 2 | 9.73 | 35.6 |
| 3 | 9.89 | 44.5 |
| 4 | 10.70 | 18.1 |
| 5 | 11.25 | 39 |
| 6 | 13.83 | 100 |
| 7 | 14.92 | 7.6 |
| 8 | 15.16 | 7.2 |
| 9 | 16.14 | 26.2 |
| 10 | 16.85 | 35.6 |
| 11 | 18.17 | 5.2 |
| 12 | 18.69 | 55.1 |
| 13 | 20.04 | 6.3 |
| 14 | 20.41 | 5.5 |
| 15 | 29.43 | 9.5 |
| 16 | 34.56 | 5.1 |

In further embodiments, the crystal form B of ginsenoside C-K has an endothermic peak of around 89±5° C. in the DSC pattern.

In another aspect of the present invention, a method for preparing the crystal form B of ginsenoside C-K is provided, comprising: (1) dissolving ginsenoside C-K in a mixed solvent consisting of N,N-dimethyl formamide and an organic solvent; (2) removing the solvent slowly by evaporation; (3) drying the resultant solid under vacuum to obtain the crystal form B of ginsenoside C-K. The organic solvent is selected from the group consisting of butyl acetate, methyl tert-butyl ether, isopropyl ether, acetone, butanone, and toluene.

In another aspect of the present invention, another method for preparing the crystal form B is provided, comprising: (1) dissolving ginsenoside C-K in an organic solvent; (2) adding water dropwise; (3) after stirring for a while, filtering the resultant suspension, and drying the filter cake under vacuum to obtain the crystal form B of ginsenoside C-K. The organic solvent is selected from the group consisting of dimethyl sulfoxide and N,N-dimethyl formamide.

In another aspect of the present invention, a crystal form C of ginsenoside C-K is provided, characterized in that there are diffraction peaks at 2θ values (°) of about 6.37, 7.96, 9.81, 12.04, 13.36, 14.94, 15.45, 15.93, 17.47, 18.63, 20.29, and 24.45 in the XRPD pattern, and preferably, these peaks are major diffraction peaks, in which the error range of 2θ value is ±0.2.

In further embodiments, the crystal form C also has diffraction peaks at 2θ values of about 5.66, 9.28, 10.87, 13.82, 14.70, 16.97, 18.98, 18.54, 19.85, 21.47, 21.83, 22.18, 22.83, 23.33, 23.76, 25.12, 26.23, 27.51, 27.90, 29.94, 32.74, 33.04 and 35.58, and preferably, these peaks are minor diffraction peaks, in which the error range of 2θ value is ±0.2.

In further embodiments, the crystal form C of ginsenoside C-K has diffraction peaks of the XRPD pattern substantially as shown in FIG. 5.

The specific data of the XRPD pattern are listed in the table below:

TABLE 3

The XRPD data of the crystal form C of ginsenoside C-K

| No. | 2θ | I % |
| --- | --- | --- |
| 1 | 5.66 | 39.1 |
| 2 | 6.37 | 8.2 |
| 3 | 7.96 | 40.4 |
| 4 | 9.28 | 100 |
| 5 | 9.81 | 8.6 |
| 6 | 10.87 | 20.4 |
| 7 | 12.04 | 53.4 |
| 8 | 13.36 | 70.9 |
| 9 | 13.82 | 5.1 |
| 10 | 14.70 | 89.8 |
| 11 | 14.94 | 100 |
| 12 | 15.45 | 58.8 |
| 13 | 15.93 | 18.6 |
| 14 | 16.95 | 34.1 |
| 15 | 17.47 | 71.4 |
| 16 | 18.63 | 16.2 |
| 17 | 18.98 | 6.9 |
| 18 | 19.54 | 49.6 |
| 19 | 19.85 | 30.2 |
| 20 | 20.29 | 52.2 |
| 21 | 21.47 | 21.6 |
| 22 | 21.83 | 9.8 |
| 23 | 22.18 | 6 |
| 24 | 22.83 | 10.6 |
| 25 | 23.33 | 14.2 |
| 26 | 23.76 | 6.7 |
| 27 | 24.45 | 6.5 |
| 28 | 25.12 | 13.8 |
| 29 | 26.23 | 9.1 |
| 30 | 27.51 | 7.8 |
| 31 | 27.90 | 8.5 |
| 32 | 29.94 | 6.2 |
| 33 | 32.74 | 6.8 |
| 34 | 33.04 | 6.8 |
| 35 | 35.58 | 6 |

In further embodiments, the crystal form C of ginsenoside C-K has an endothermic peak of around 129±5° C. in the DSC pattern.

In another aspect of the present invention, a method for preparing the crystal form C of ginsenoside C-K is provided, comprising: (1) dissolving ginsenoside C-K in an organic solvent; (2) removing the solvent slowly by evaporation; (3) drying the resultant solid under vacuum to obtain the crystal form C of ginsenoside C-K. The organic solvent is selected from the group consisting of ethanol, ethyl acetate, isopropyl acetate or a combination thereof.

In another aspect of the present invention, a crystal form E of ginsenoside C-K is provided, characterized in that there are diffraction peaks at 2θ values (°) of about 6.14, 6.71, 12.38, 13.58, 15.41, and 16.93 in the XRPD pattern, and preferably, these peaks are major diffraction peaks, in which the error range of 2θ value is ±0.2.

In further embodiments, the crystal form E also has diffraction peaks at 2θ values of about 7.74, 9.39, 10.44, 19.44, 20.07, 20.70, and 22.24, and preferably, these peaks are minor diffraction peaks, in which the error range of 2θ value is ±0.2.

In further embodiments, the crystal form E of ginsenoside C-K has diffraction peaks of the XRPD pattern substantially as shown in FIG. 7.

The specific data of the XRPD pattern are listed in the table below:

TABLE 4

The data of XRPD diffraction angles of the crystal form E of ginsenoside C-K

| No. | 2θ | I % |
| --- | --- | --- |
| 1 | 6.14 | 100 |
| 2 | 6.71 | 41.2 |
| 3 | 7.74 | 8.3 |
| 4 | 9.39 | 7.4 |
| 5 | 10.44 | 8.6 |
| 6 | 12.38 | 28.5 |
| 7 | 13.58 | 25.3 |
| 8 | 15.41 | 29.7 |
| 9 | 16.93 | 21.8 |
| 10 | 19.44 | 7.8 |
| 11 | 20.07 | 4.8 |
| 12 | 20.70 | 5.7 |
| 13 | 22.24 | 4.9 |

In another aspect of the present invention, a method for preparing the crystal form E of ginsenoside C-K is provided, comprising: (1) dissolving ginsenoside C-K in methanol; (2) adding water dropwise; (3) after stirring for a while, filtering the resultant suspension, and drying the filter cake under vacuum to obtain the crystal form E of ginsenoside C-K.

In another aspect of the present invention, a crystal form F of ginsenoside C-K is provided, characterized in that there are diffraction peaks at 2θ values (°) of about 5.65, 6.87, 9.02, 11.23, 12.31, 12.65, 13.42, 14.70, 15.75, 17.15, 20.50, 20.80, 22.50, and 26.60 in the XRPD pattern, and preferably, these peaks are major diffraction peaks, in which the error range of 2θ value is ±0.2.

In further embodiments, the crystal form F also has diffraction peaks at 2θ values of about 11.74, 18.35, 19.10, 19.66, 21.59, 21.98, 23.76, and 24.73, and preferably, these peaks are minor diffraction peaks, in which the error range of 2θ value is ±0.2.

In further embodiments, the crystal form F of ginsenoside C-K has diffraction peaks of the XRPD pattern substantially as shown in FIG. 8.

The specific data of the XRPD pattern are listed in the table below:

TABLE 5

The data of XRPD diffraction angles of the crystal form F of ginsenoside C-K

| No. | 2θ | I % |
| --- | --- | --- |
| 1 | 5.65 | 52.7 |
| 2 | 6.87 | 89 |
| 3 | 9.02 | 19.2 |
| 4 | 11.23 | 45.2 |
| 5 | 11.74 | 8.9 |
| 6 | 12.31 | 7 |
| 7 | 12.65 | 7 |
| 8 | 13.42 | 13.7 |
| 9 | 14.70 | 100 |
| 10 | 15.75 | 50.9 |
| 11 | 17.15 | 22.9 |
| 12 | 18.35 | 10.2 |
| 13 | 19.10 | 7.2 |
| 14 | 19.66 | 7.6 |
| 15 | 20.50 | 11.8 |
| 16 | 20.80 | 13.1 |
| 17 | 21.59 | 6 |
| 18 | 21.98 | 6.7 |
| 19 | 22.50 | 19.1 |
| 20 | 23.76 | 12.2 |
| 21 | 24.73 | 9.2 |
| 22 | 26.60 | 11.2 |

In further embodiments, the crystal form F of ginsenoside C-K has an endothermic peak at 117±5° C. in the DSC pattern.

In another aspect of the present invention, a method for preparing the crystal form F of ginsenoside C-K is provided, comprising: (1) dissolving ginsenoside C-K in a mixed solvent consisting of 1-methyl-2-pyrrolidone and 1,2-dichloroethane; (2) removing the solvent slowly by evaporation; (3) drying the resultant solid under vacuum to obtain the crystal form F of ginsenoside C-K.

In another aspect of the present invention, a crystal form I of ginsenoside C-K is provided, characterized in that it is an ethanol dihydrate, which belongs to monoclinic system, and has the following cell parameters: a=11.775(2) Å, b=12.456(3) Å, c=14.179(3) Å, α=γ=90.00°, β=98.00(3)°, and cell volume V=2059.4(7) Å$^3$.

In another aspect of the present invention, a method for preparing the crystal form I of ginsenoside C-K is provided, comprising: (1) dissolving ginsenoside C-K in ethanol at room temperature; (2) evaporating the solution slowly at room temperature to obtain a single crystal of the crystal form I.

In another aspect of the present invention, a crystal form K of ginsenoside C-K is provided, characterized in that it is an isopropanol dihydrate, which belongs to monoclinic system with the space group of $P2_1$, and has the following cell parameters: a=11.643(2) Å, b=12.385(3) Å, c=14.365(3) Å, α=γ=90.00°, β=96.06(3)°, cell volume V=2059.8(7) Å$^3$, and the number of asymmetric unit in the cell Z=2.

In another aspect of the present invention, a method for preparing the crystal form K of ginsenoside C-K is provided, comprising: (1) dissolving ginsenoside C-K in isopropanol and water at an increased temperature; (2) after cooling, adding water dropwise; (3) filtering and drying the solid under vacuum to obtain the crystal form K of ginsenoside C-K.

In another aspect of the present invention, a method for preparing the crystal form K of ginsenoside C-K is provided, comprising: (1) dissolving ginsenoside C-K in isopropanol or a mixed solvent of isopropanol and another solvent, wherein the isopropanol may contain a small amount of water, for example, its water content is preferably greater than 0 but <=1% (v/v), where there is no water contained in said another solvent, for example, isopropanol of chemically pure grade or analytical grade; (2) evaporating the solvent slowly; (3) drying the solid under vacuum to obtain the crystal form K of ginsenoside C-K. Said another solvent is selected from the group consisting of pentane or cyclohexane etc., and its amount used can be appropriately determined by those skilled in the art. Preferably, the volume ratio of isopropanol and said another solvent is from 1:10 to 10:1, and more preferably from 1:5 to 1:1, and most preferably 1:3.

In another aspect of the present invention, a crystal form O of ginsenoside C-K is provided, which is amorphous and characterized in that there is no obvious diffraction peak in XRPD pattern, substantially as shown in FIG. 18.

In another aspect of the present invention, a method for preparing the crystal form O of ginsenoside C-K is provided, comprising: (1) dissolving ginsenoside C-K in an organic solvent at an increased temperature; (2) removing the solvent quickly by evaporation; (3) drying the resultant solid under vacuum to obtain the crystal form O of ginsenoside C-K. The organic solvent is selected from the group consisting of methanol, ethanol, ethyl acetate, acetone, chloroform, water and a combination thereof.

In another aspect of the present invention, a method for preparing the crystal form O of ginsenoside C-K is additionally provided, comprising: (1) dissolving ginsenoside C-K in an organic solvent; (2) adding water quickly and stirring; (3) filtering the suspension, and drying under vacuum to obtain the crystal form O of ginsenoside C-K. The organic solvent is selected from the group consisting of methanol, ethanol, acetone, NMP, THF, n-propanol, isopropanol, n-butanol, n-pentanol, DMF, DMSO, and acetonitrile.

In another aspect of the present invention, a crystal form L of ginsenoside C-K is provided, which is characterized in that there are diffraction peaks at 2θ values (°) of about 5.46, 6.91, 10.81, 11.29, 12.61, 13.76, 14.15, 15.49, 16.44, 17.29, 18.99, and 23.21 in the XRPD pattern, and preferably, these peaks are major diffraction peaks, in which the error range of 2θ value is ±0.2.

In further embodiments, the crystal form L also has diffraction peaks at 2θ values of about 9.57, 9.95, 15.22, and 28.91, and preferably, these peaks are minor diffraction peaks, in which the error range of 2θ value is ±0.2.

In further embodiments, the crystal form L of ginsenoside C-K has diffraction peaks of the XRPD pattern substantially as shown in FIG. 15.

The specific data of the XRPD pattern are listed in the table below:

TABLE 6

The data of XRPD diffraction angles of the crystal form L of ginsenoside C-K

| No. | 2θ | I % |
|---|---|---|
| 1 | 5.46 | 30.5 |
| 2 | 6.91 | 100 |
| 3 | 9.57 | 3.8 |
| 4 | 9.95 | 4.6 |
| 5 | 10.81 | 38.1 |
| 6 | 11.29 | 12.6 |
| 7 | 12.61 | 12.1 |
| 8 | 13.76 | 63.8 |
| 9 | 14.15 | 13.7 |
| 10 | 15.22 | 12.1 |
| 11 | 15.49 | 21.8 |
| 12 | 16.44 | 16.9 |
| 13 | 17.29 | 39.6 |
| 14 | 18.99 | 18 |
| 15 | 23.21 | 10.6 |
| 16 | 28.91 | 4.5 |

In another aspect of the present invention, a method for preparing the crystal form L of ginsenoside C-K is provided, comprising: (1) dissolving ginsenoside C-K in methanol at an increased temperature; (2) after cooling, adding water dropwise slowly; (3) filtering and drying the solid under vacuum to obtain the crystal form L of ginsenoside C-K.

In another aspect of the present invention, a crystal form M of ginsenoside C-K is provided, characterized in that there are diffraction peaks at 2θ values (°) of about 6.18, 7.64, 9.37, 10.44, 11.68, 12.41, 13.83, 14.25, 15.37, 16.95, 18.71, 20.01, and 22.26 in the XRPD pattern, and preferably, these peaks are major diffraction peaks, in which the error range of 2θ value is ±0.2.

In further embodiments, the crystal form M also has diffraction peaks at 2θ values of about 17.64, 19.38, 20.68, 21.04, and 23.92, and preferably, these peaks are minor diffraction peaks, in which the error range of 2θ value is ±0.2.

In further embodiments, the crystal form M of ginsenoside C-K has diffraction peaks of the XRPD pattern substantially as shown in FIG. 16.

The specific data of the XRPD pattern are listed in the table below:

TABLE 7

The data of XRPD diffraction angles of the crystal form M of ginsenoside C-K

| No. | 2θ | I % |
|---|---|---|
| 1 | 6.18 | 100 |
| 2 | 7.64 | 20.9 |
| 3 | 9.37 | 16.8 |
| 4 | 10.44 | 36.5 |
| 5 | 11.68 | 8.5 |
| 6 | 12.41 | 23.9 |
| 7 | 13.83 | 19.2 |
| 8 | 14.25 | 10.2 |
| 9 | 15.37 | 29 |
| 10 | 16.95 | 63.2 |
| 11 | 17.64 | 6.4 |
| 12 | 18.71 | 15.6 |
| 13 | 19.38 | 6.8 |
| 14 | 20.01 | 10.7 |
| 15 | 20.68 | 5.4 |
| 16 | 21.04 | 5.3 |
| 17 | 22.26 | 11.1 |
| 18 | 23.92 | 5.4 |

In another aspect of the present invention, a method for preparing the crystal form M of ginsenoside C-K is provided, comprising: (1) dissolving ginsenoside C-K in a mixed solvent of ethanol and benzene; (2) removing the solvent slowly by evaporation; (3) drying the resultant solid under vacuum to obtain the crystal form M of ginsenoside C-K.

In another aspect of the present invention, a crystal form N of ginsenoside C-K is provided, characterized in that there are diffraction peaks at 2θ values (°) of about 3.40, 4.40, 6.51, 6.77, 8.11, 9.38, 10.16, 10.56, 13.11, 14.58, 15.35, 16.28, 17.64, and 18.43 in the XRPD pattern, and preferably, these peaks are major diffraction peaks, in which the error range of 2θ value is ±0.2.

In further embodiments, the crystal form N also has diffraction peaks at 2θ values of about 12.29, 16.99, 20.39, 23.60, 24.51, and 25.28, and preferably, these peaks are minor diffraction peaks, in which the error range of 2θ value is ±0.2.

In further embodiments, the crystal form N of ginsenoside C-K has diffraction peaks of the XRPD pattern substantially as shown in FIG. 17.

The specific data of the XRPD pattern are listed in the table below:

TABLE 8

The data of XRPD diffraction angles of the crystal form N of ginsenoside C-K

| No. | 2θ | I % |
|---|---|---|
| 1 | 3.40 | 15.6 |
| 2 | 4.40 | 100 |
| 3 | 6.51 | 54.1 |
| 4 | 6.77 | 71.1 |
| 5 | 8.11 | 12.1 |
| 6 | 9.38 | 37.6 |
| 7 | 10.16 | 64.6 |
| 8 | 10.56 | 27.4 |
| 9 | 12.29 | 8.7 |
| 10 | 13.11 | 62.5 |
| 11 | 14.58 | 23.1 |
| 12 | 15.35 | 33.2 |
| 13 | 16.28 | 24.8 |

TABLE 8-continued

The data of XRPD diffraction angles of the crystal form N of ginsenoside C-K

| No. | 2θ | I % |
|-----|-------|------|
| 14 | 16.99 | 10.2 |
| 15 | 17.64 | 20.2 |
| 16 | 18.43 | 10.2 |
| 17 | 20.39 | 9.3 |
| 18 | 23.60 | 7.2 |
| 19 | 24.51 | 6.5 |
| 20 | 25.28 | 10 |

In another aspect of the present invention, a method for preparing the crystal form N of ginsenoside C-K is provided, comprising: (1) dissolving ginsenoside C-K in a mixture of acetonitrile and water at an increased temperature; (2) after cooling, adding water dropwise slowly; (3) filtering and drying the solid under vacuum to obtain the crystal form N of ginsenoside C-K. Preferably, the temperature for cooling is from 4 to 20° C.

DETAILED DESCRIPTION OF THE INVENTION

Figure 1:
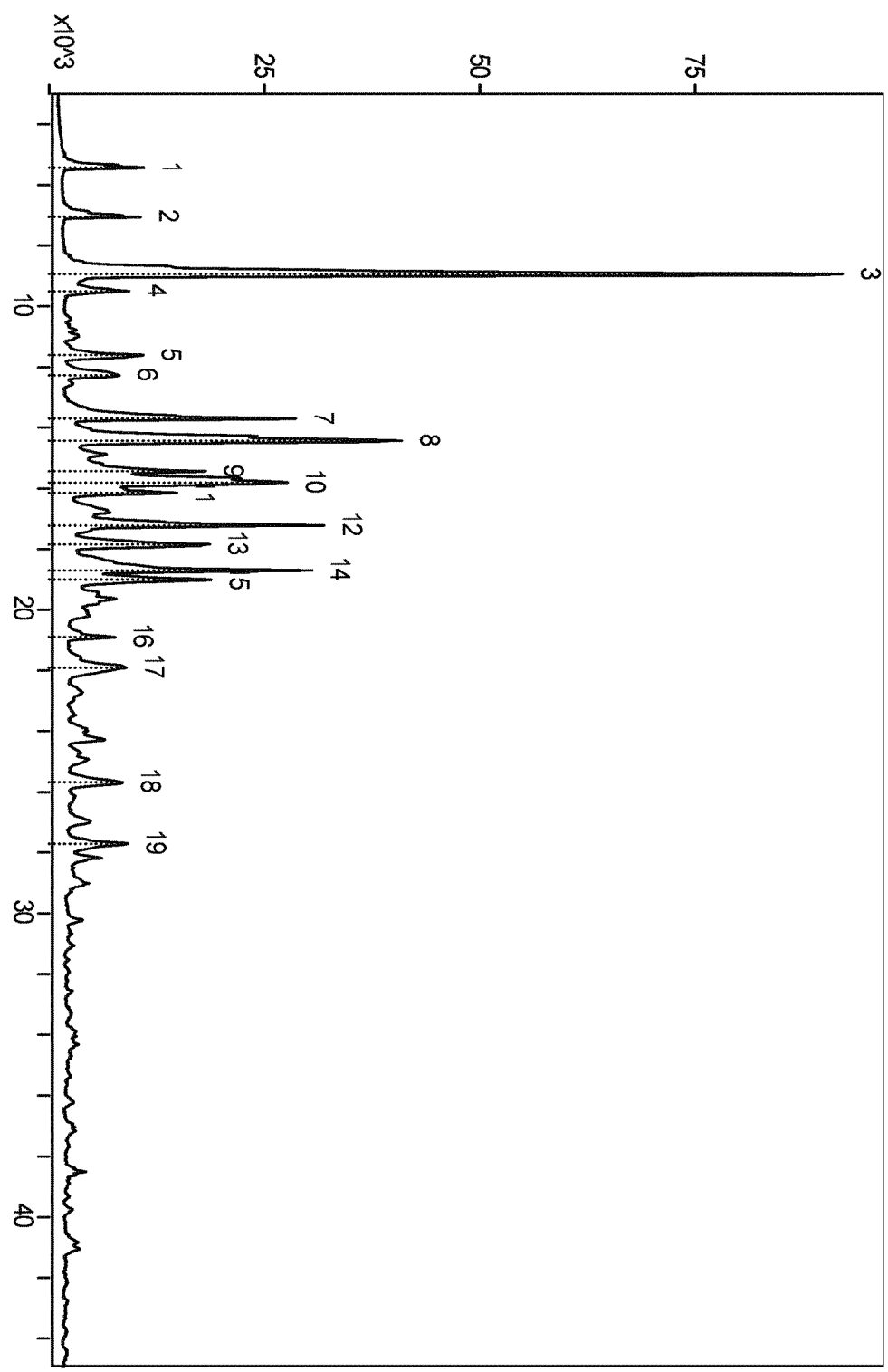
FIG. 1 is an X-ray powder diffraction pattern of the crystal form A of ginsenoside C-K.
Figure 2:
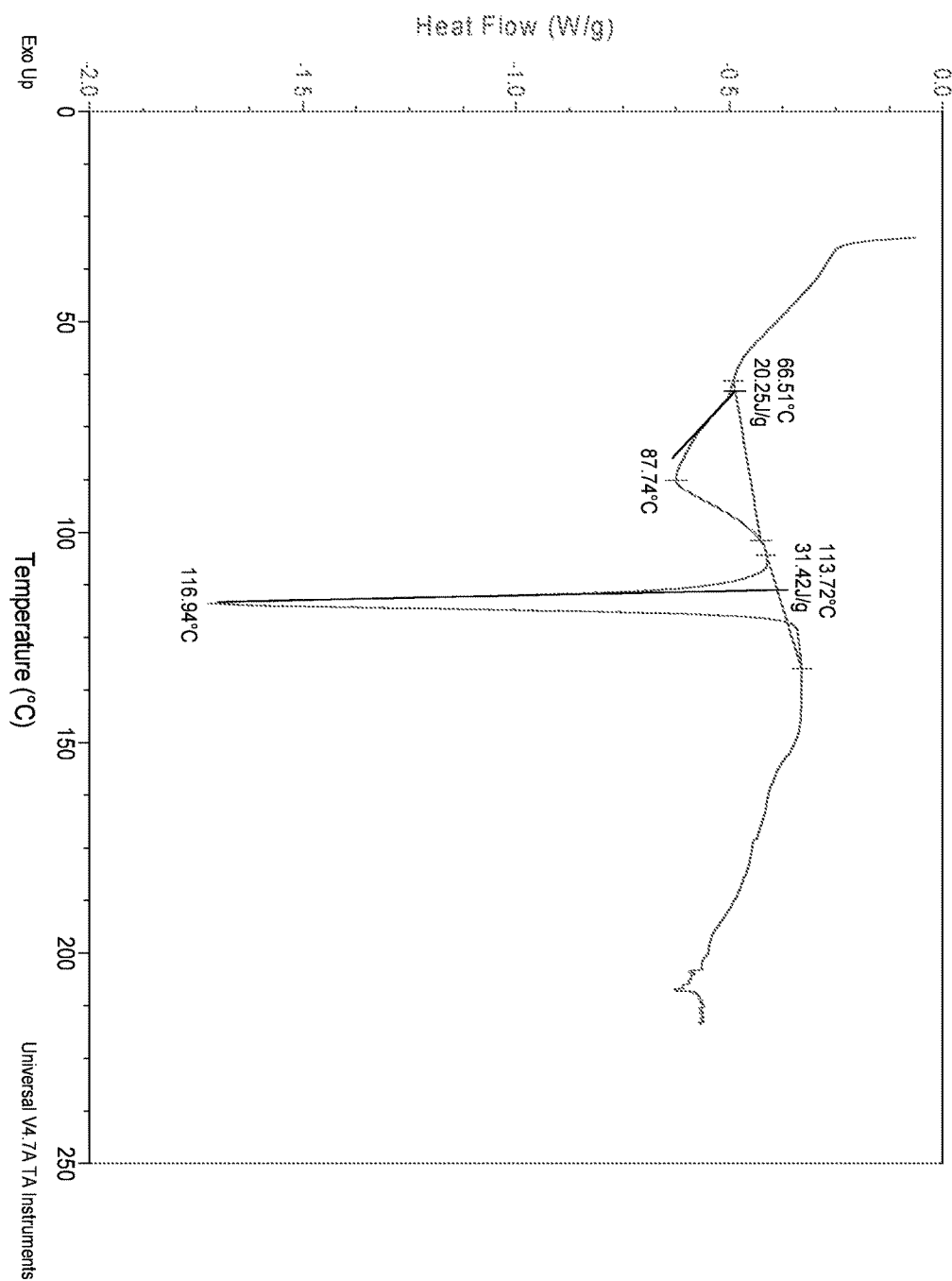
FIG. 2 is a DSC pattern of the crystal form A of ginsenoside C-K.
Figure 3:
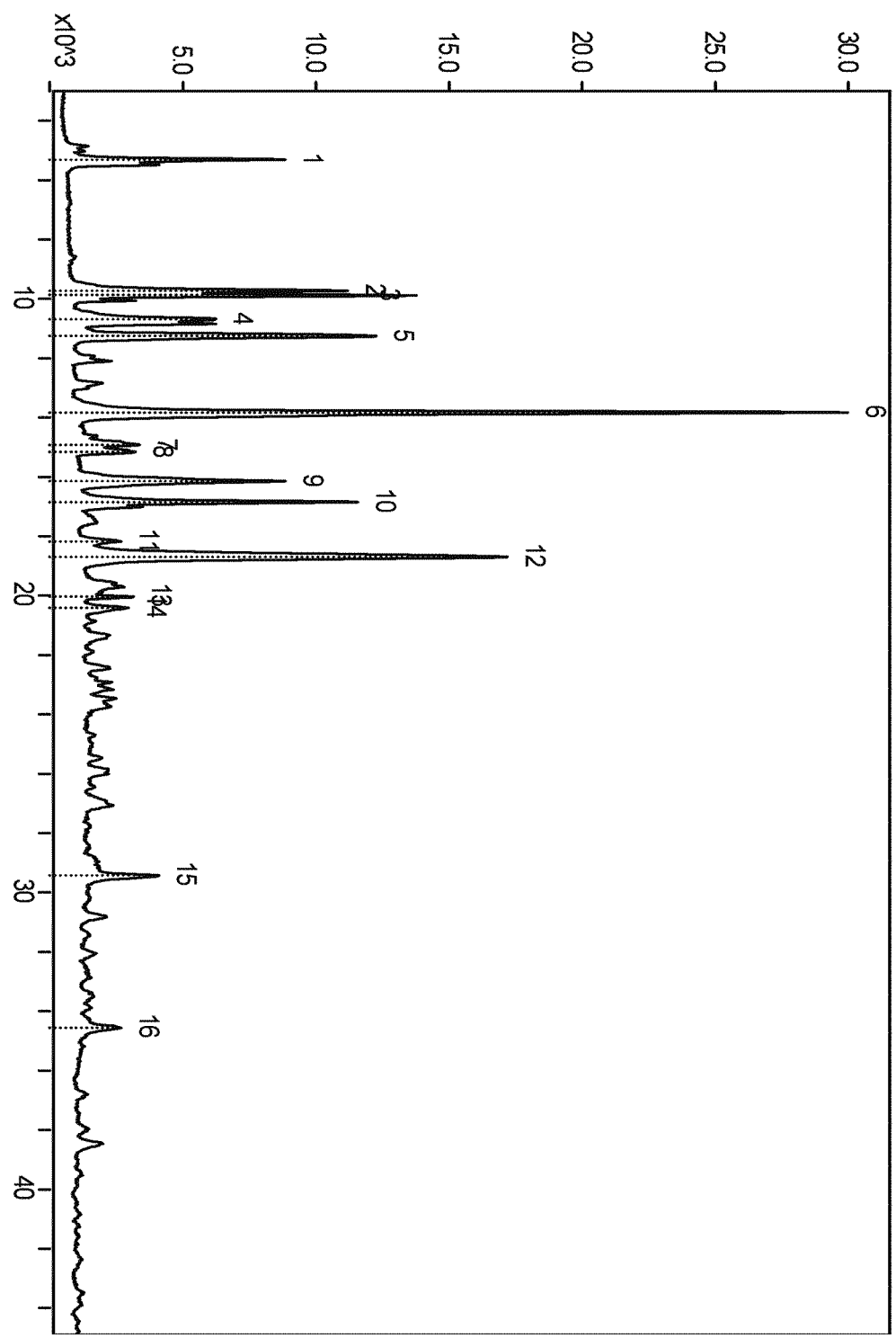
FIG. 3 is an X-ray powder diffraction pattern of the crystal form B of ginsenoside C-K.
Figure 4:
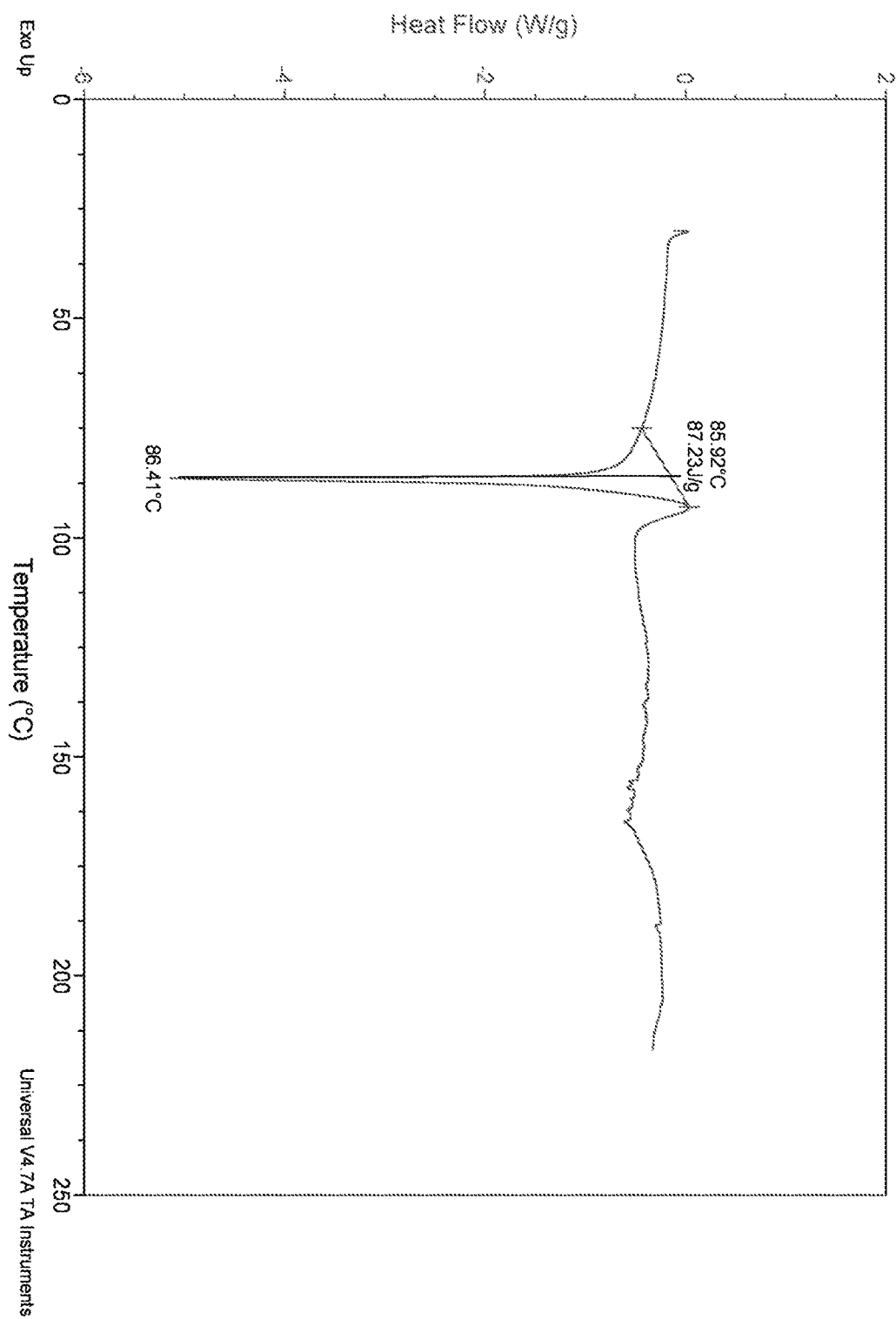
FIG. 4 is a DSC pattern of the crystal form B of ginsenoside C-K.
Figure 5:
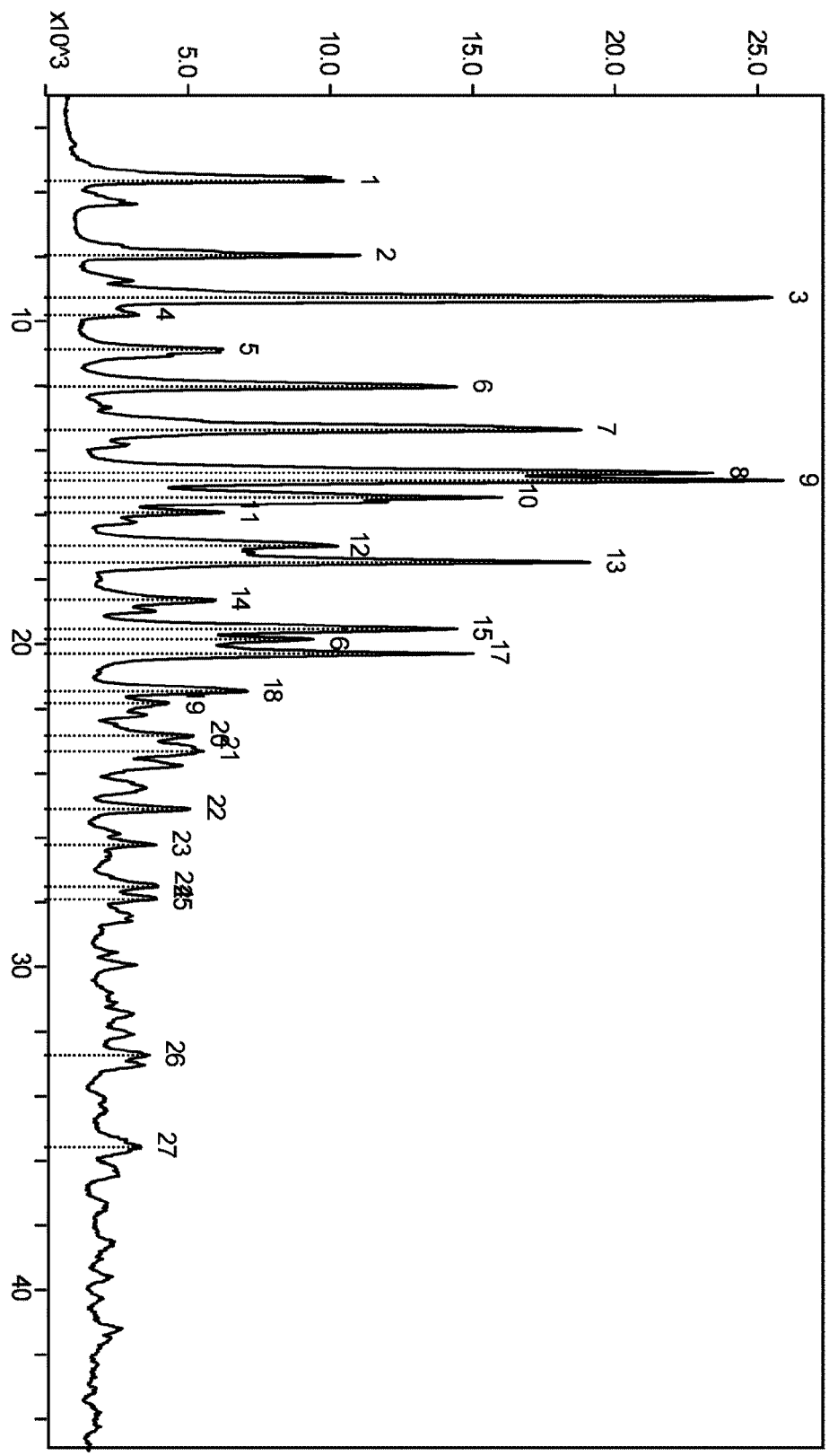
FIG. 5 is an X-ray powder diffraction pattern of the crystal form C of ginsenoside C-K.
Figure 6:
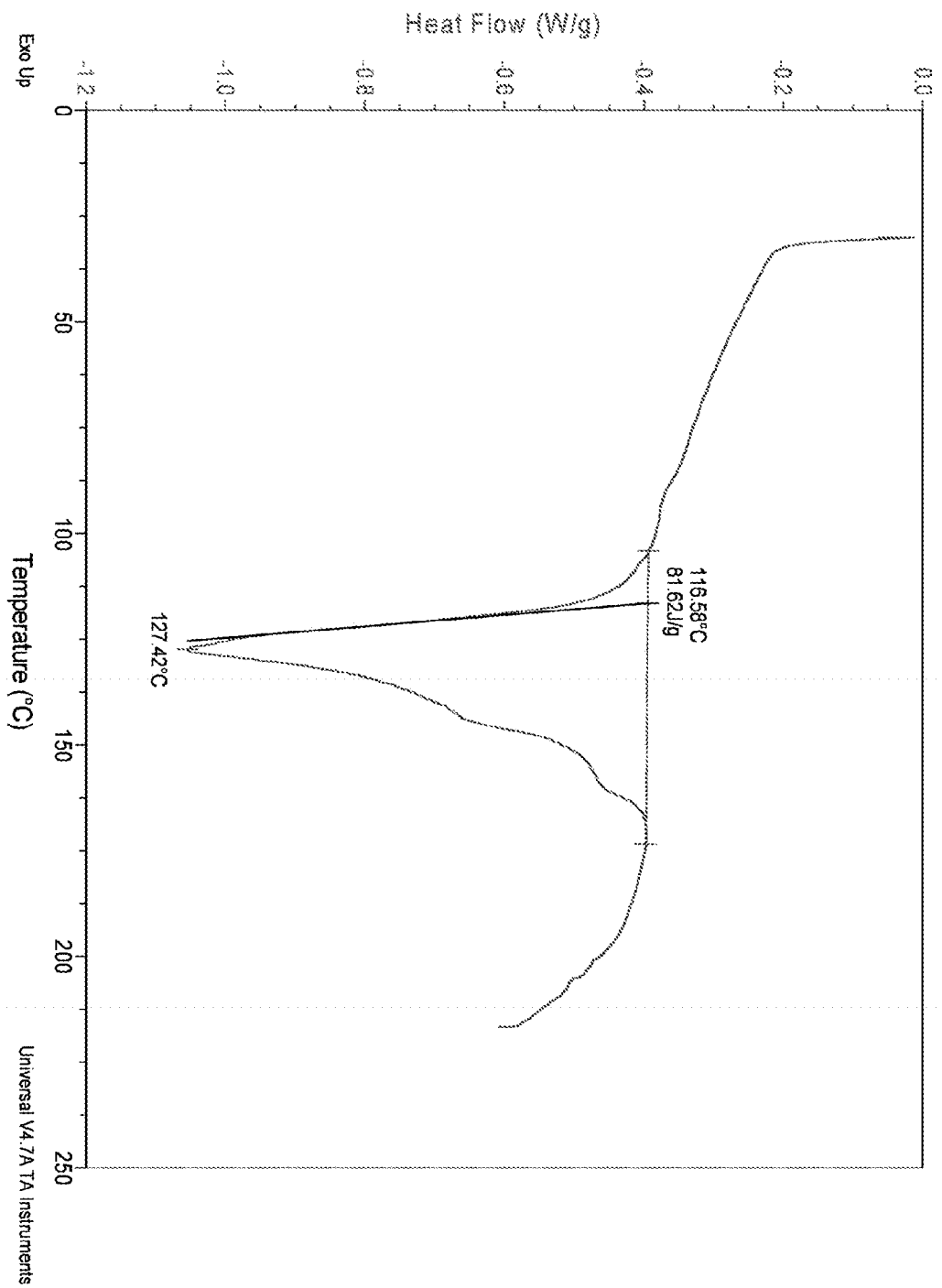
FIG. 6 is a DSC pattern of the crystal form C of ginsenoside C-K.
Figure 7:
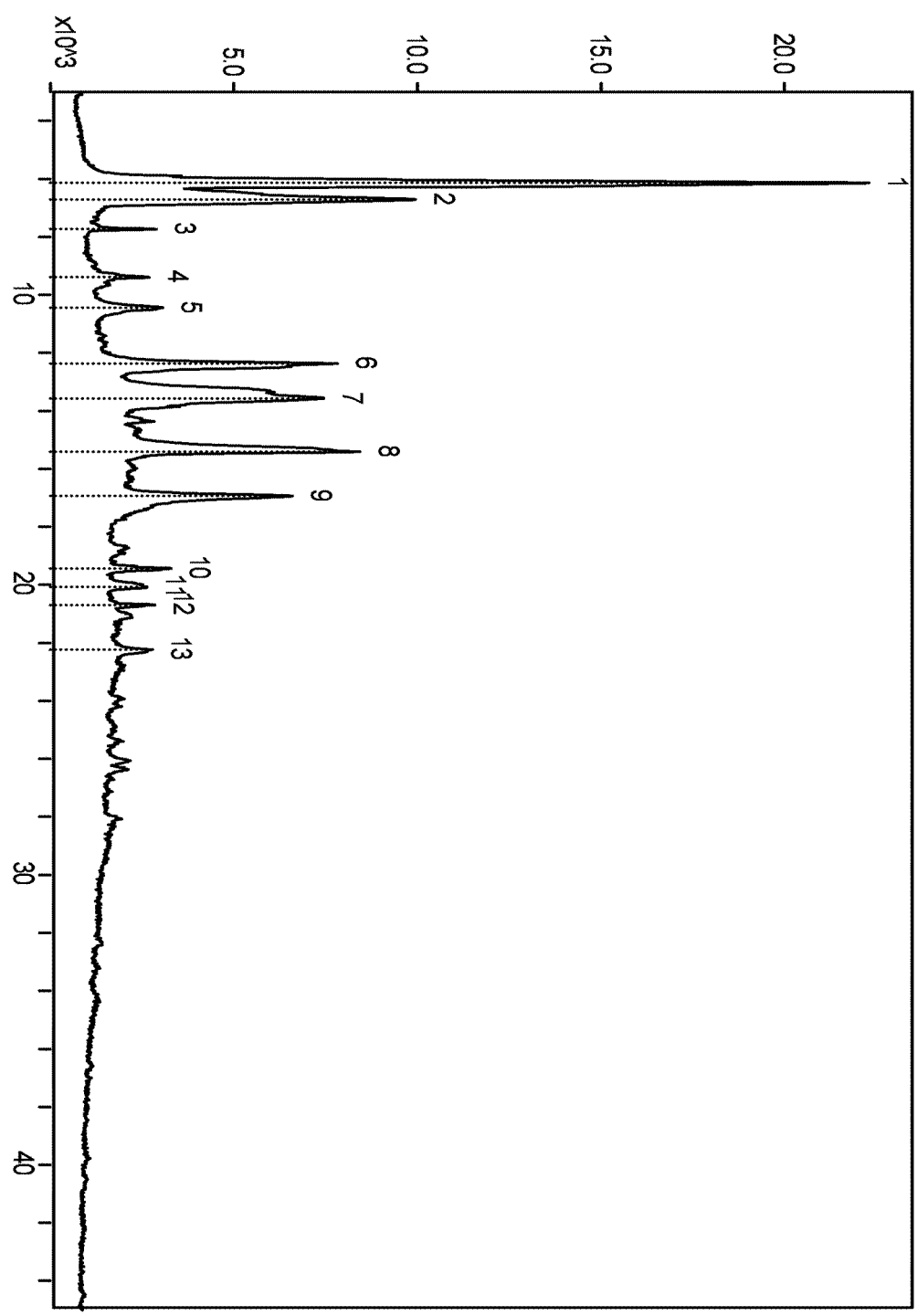
FIG. 7 is an X-ray powder diffraction pattern of the crystal form E of ginsenoside C-K.
Figure 8:
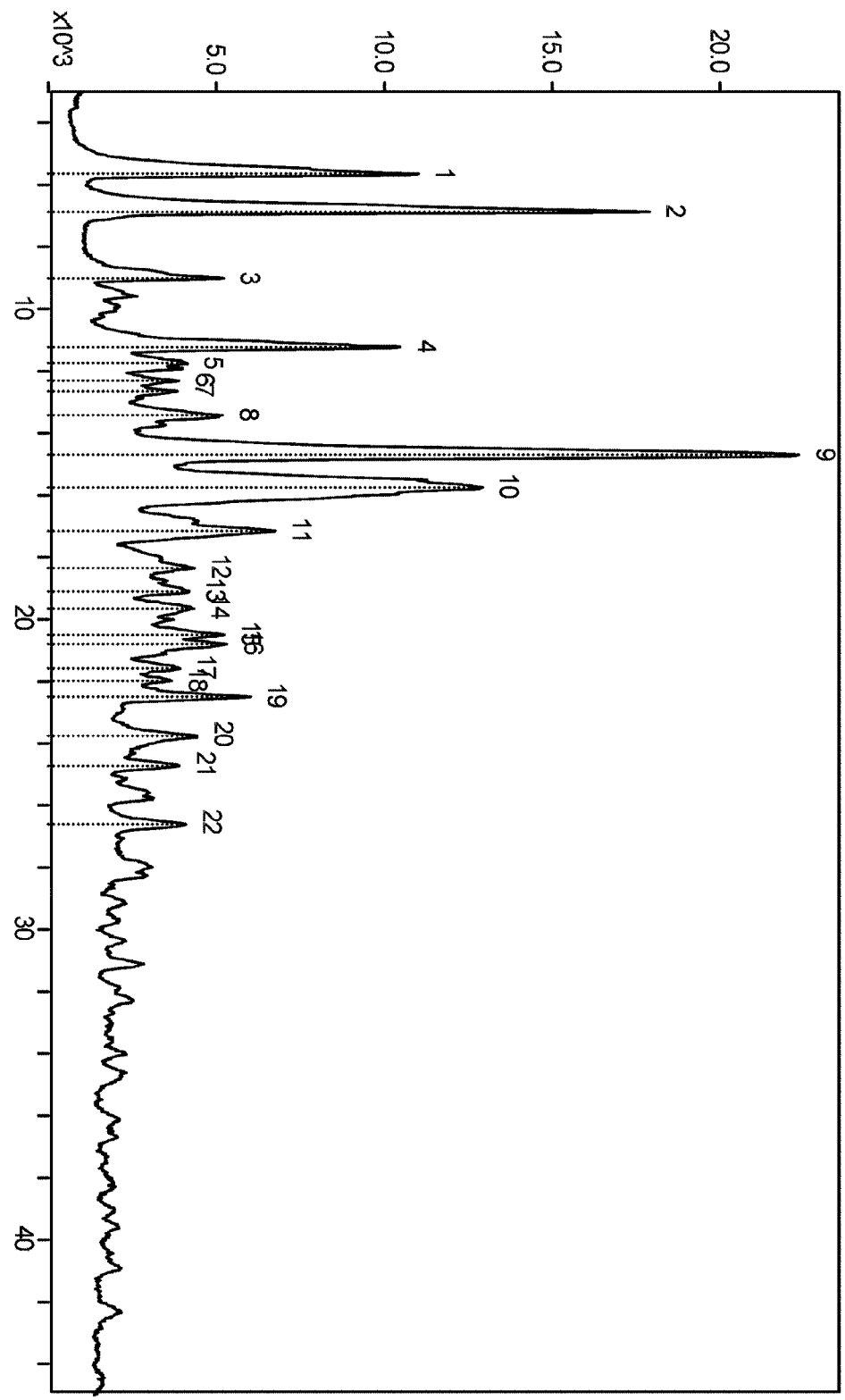
FIG. 8 is an X-ray powder diffraction pattern of the crystal form F of ginsenoside C-K.
Figure 9:
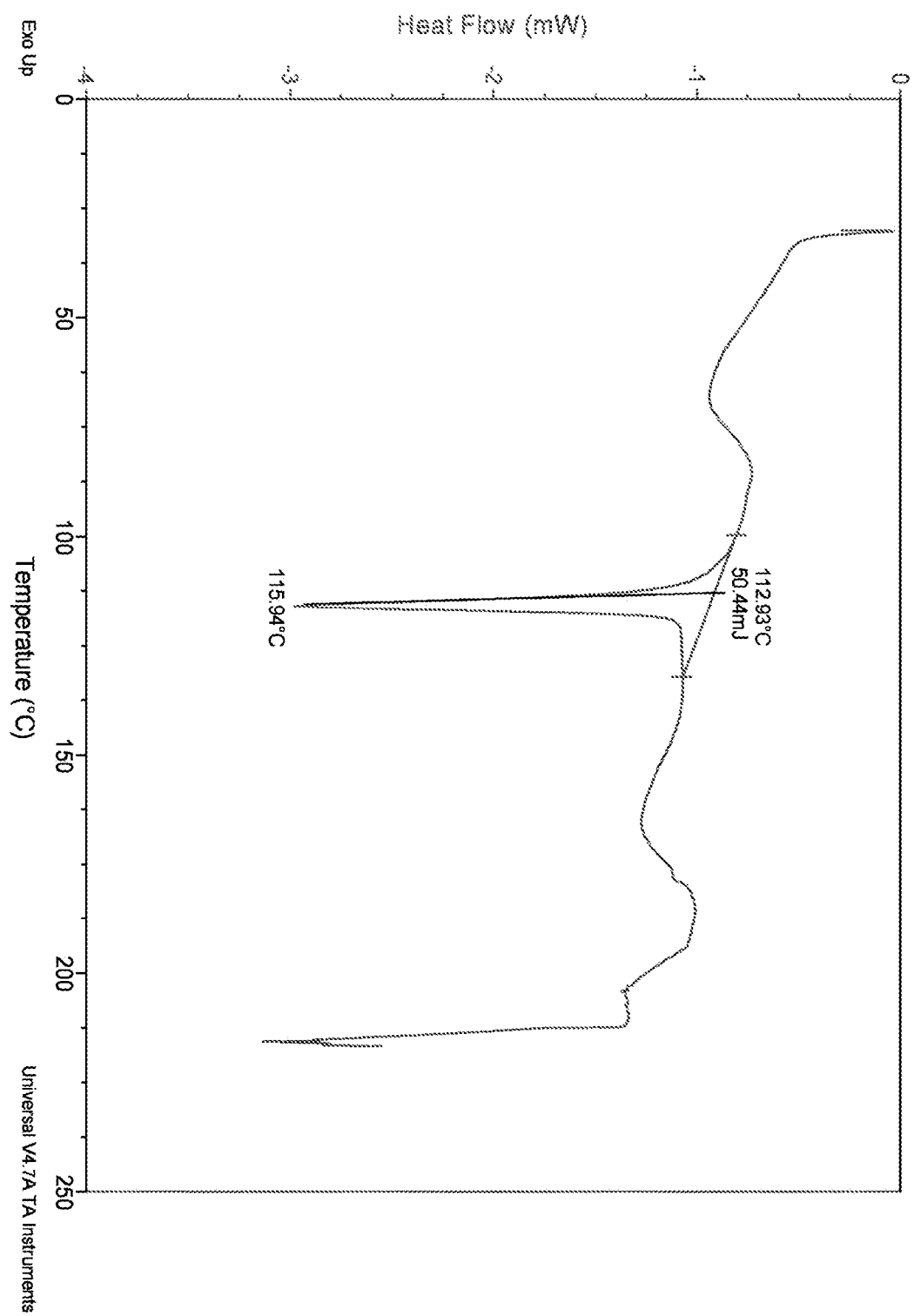
FIG. 9 is a DSC pattern of the crystal form F of ginsenoside C-K.
Figure 10:
FIG. 10 is a simulated XRPD pattern of the crystal form I of ginsenoside C-K.
Figure 11:
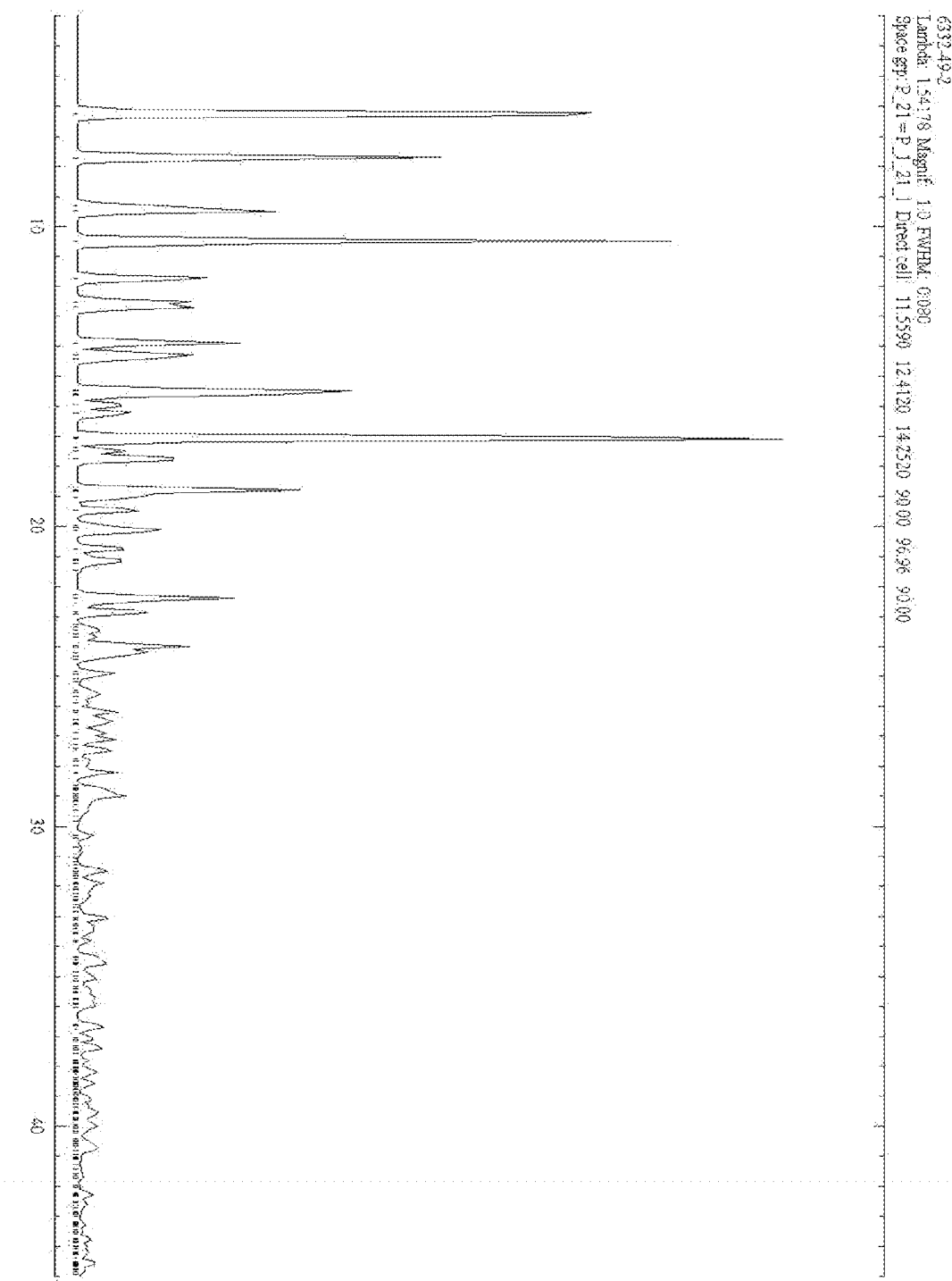
FIG. 11 is a simulated XRPD pattern of the crystal form J of ginsenoside C-K.
Figure 12:
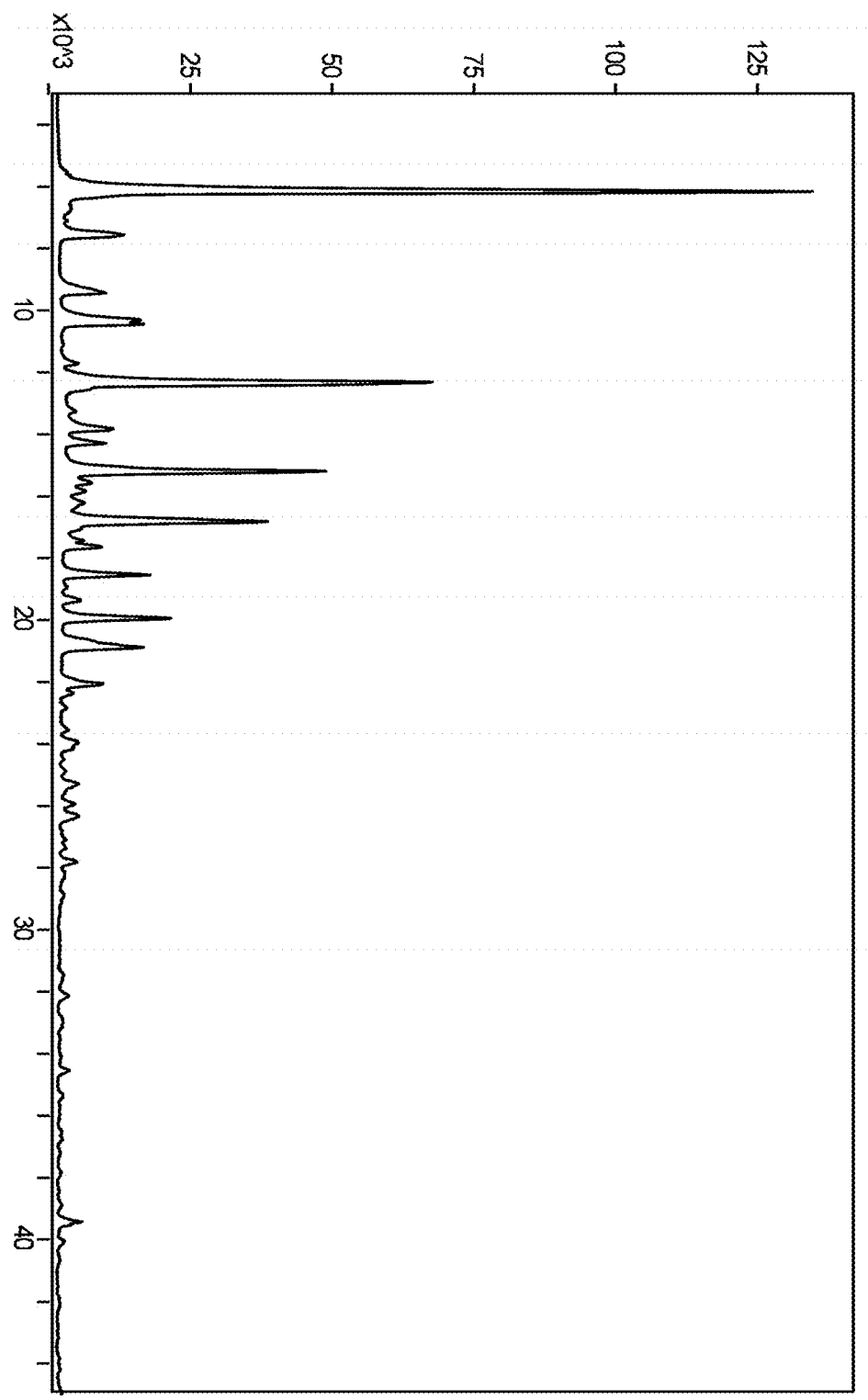
FIG. 12 is an X-ray powder diffraction pattern of the crystal form K of ginsenoside C-K.

The crystal form O of ginsenoside C-K is prepared using the crystal form G of ginsenoside C-K as raw material, whereas the rest crystal forms of ginsenoside C-K are prepared using the crystal form O of ginsenoside C-K as raw material.

All reagents used in the examples are of analytical grade.

1. Preparation of the Crystal Form a of Ginsenoside C-K

Example 1

10 g ginsenoside C-K was placed in a container, into which 100 ml 1-methyl-2-pyrrolidone was added and evaporated slowly until solid occurred. Subsequently, it was filtered, washed twice using 60 ml distilled water, and dried at room temperature under vacuum to obtain the crystal form A of ginsenoside C-K.

Example 2

1 g ginsenoside C-K was placed in a container, into which 10 ml 1-methyl-2-pyrrolidone and 80 ml acetone were added. After dissolution by stirring, it was evaporated slowly until solid occurred. Subsequently, it was filtered, washed twice using 20 ml distilled water, and dried at room temperature under vacuum to obtain the crystal form A of ginsenoside C-K.

Example 3

4 g ginsenoside C-K was placed in a container, into which 40 ml 1-methyl-2-pyrrolidone was added. After dissolution, 60 ml water was slowly added dropwise, and stirred for 1 h. Subsequently, it was filtered, washed twice using 40 ml distilled water, and dried at room temperature under vacuum to obtain the crystal form A of ginsenoside C-K.

Example 4

4 g ginsenoside C-K was placed in a container, into which 40 ml 1-methyl-2-pyrrolidone was added. After dissolution, 100 ml isopropyl ether was slowly added dropwise, and stirred for 1 h. Subsequently, it was filtered, washed twice using 40 ml distilled water, and dried at room temperature under vacuum to obtain the crystal form A of ginsenoside C-K.

2. Preparation of the Crystal Form B of Ginsenoside C-K

Example 5

3 g ginsenoside C-K was placed in a container, into which 10 ml DMF was added followed by the addition of 90 ml butyl acetate. Subsequently, it was stirred and evaporated slowly until solid occurred. It was then filtered, washed twice using 60 ml distilled water, and dried at room temperature under vacuum to obtain the crystal form B of ginsenoside C-K.

Example 6

3 g ginsenoside C-K was placed in a container, into which 10 ml DMF was added followed by the addition of 90 ml butanone. Subsequently, it was stirred and evaporated slowly until solid developed. It was then filtered, washed twice using 60 ml distilled water, and dried at room temperature under vacuum to obtain the crystal form B of ginsenoside C-K.

Example 7

3 g ginsenoside C-K was placed in a container, into which 10 ml DMF was added followed by the addition of 90 ml methyl tert-butyl ether. Subsequently, it was stirred and evaporated slowly until solid developed. It was then filtered, washed twice using 60 ml distilled water, and dried at room temperature under vacuum to obtain the crystal form B of ginsenoside C-K.

Example 8

4 g ginsenoside C-K was placed in a container, into which 50 ml dimethyl sulfoxide and 10 ml water were added. After dissolution by stirring, 90 ml water was slowly added dropwise, and solid developed. After stirring for 2 h, it was filtered, washed twice using 60 ml distilled water, and dried under vacuum to obtain the crystal form B of ginsenoside C-K.

3. Preparation of the Crystal Form C of Ginsenoside C-K

Example 9

9 g ginsenoside C-K was placed in a container, into which 30 ml ethanol was added. After dissolution by stirring, it was evaporated slowly until solid occurred. It was then filtered, washed twice using 60 ml distilled water, and dried at room temperature under vacuum to obtain the crystal form C of ginsenoside C-K.

Example 10

3 g ginsenoside C-K was placed in a container, into which 10 ml ethanol was added followed by the addition of 90 ml isopropyl acetate. After dissolution by stirring, it was evaporated slowly until solid occurred. It was then filtered, washed twice using 60 ml distilled water, and dried at room temperature under vacuum to obtain the crystal form C of ginsenoside C-K.

4. Preparation of the Crystal Form E of Ginsenoside C-K

Example 11

10 g ginsenoside C-K was placed in a container, into which 150 ml methanol was added and the temperature was increased to 40° C. After dissolution by stirring, the solution was cooled down to 25° C., and it was still clear. Subsequently, 95 ml water was added dropwise at a rate of 15 ml/min. It was then filter by suction to obtain crystal, which was dried at 50° C. for 24 h in an oven to obtain the crystal form E of ginsenoside C-K.

5. Preparation of the Crystal Form F of Ginsenoside C-K

Example 12

1 g ginsenoside C-K was placed in a container, into which 10 ml NMP and 80 ml 1,2-dichloroethane were added. After dissolution by stirring, it was evaporated slowly until solid occurred. It was then filtered, washed twice using 20 ml distilled water, and dried at room temperature under vacuum to obtain the crystal form F of ginsenoside C-K.

6. Preparation of the Crystal Form I of Ginsenoside C-K

Example 13

500 mg ginsenoside C-K was dissolved in 50 ml ethanol at room temperature. Subsequently, the solution was evaporated slowly at room temperature for 1 day to obtain the crystal form I of the monocrystal.

7. Preparation of the Crystal Form K of Ginsenoside C-K

Example 14

2 g ginsenoside C-K was placed in a container, into which 20 ml isopropanol (analytical grade) was added. After dissolution by stirring, a portion of the solvent was removed by evaporation slowly and the solution was filtered to obtain the solid. Subsequently, the resultant solid was dried at room temperature under vacuum to obtain the crystal form K of ginsenoside C-K.

Example 15

Figure 13:
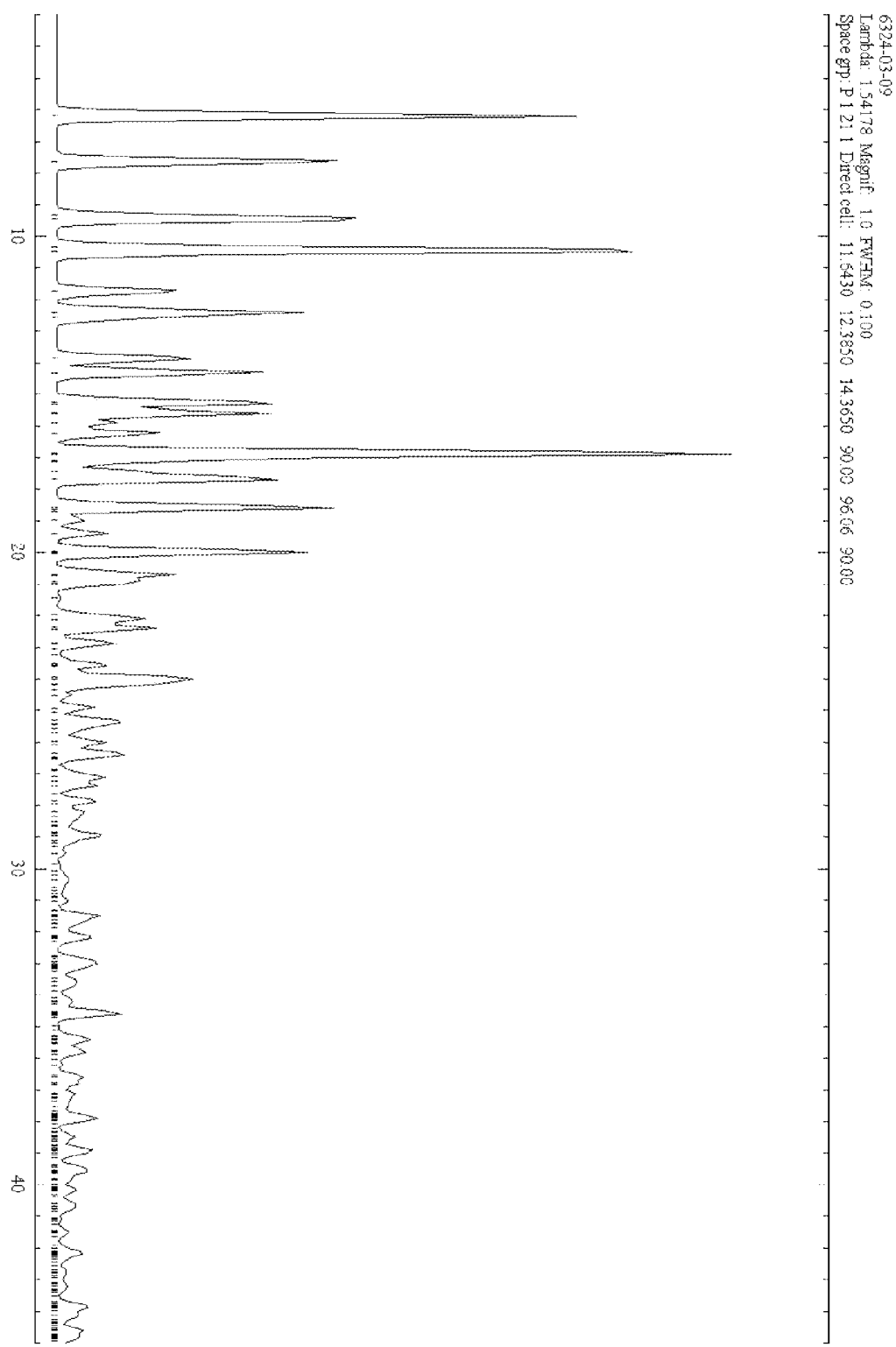
FIG. 13 is a simulated X-ray powder diffraction pattern of a single crystal of the crystal form K obtained in Example 14.

2 g ginsenoside C-K was placed in a container, into which 10 isopropanol (analytical grade) was added followed by the addition of 30 ml cyclohexane. After dissolution by stirring, the solution was filtered, and the filtrate stood for a while until bulk crystal developed. The resultant crystal was detected by single-crystal X-ray diffraction, and the following results were obtained: the crystal belongs to monoclinic system with the space group of $P2_1$, and has the cell parameters: a=11.643(2) Å, b=12.385(3) Å, c=14.365(3) Å, $\alpha=\gamma=90.00°$, $\beta=96.06(3)°$, cell volume V=2059.8(7) Å$^3$, and the number of asymmetric unit in the cell Z=2. Its simulated XRPD pattern was shown in FIG. 13.

Example 16

2 g ginsenoside C-K was placed in a container, into which 10 ml isopropanol (analytical grade) was added followed by the addition of 30 ml n-pentane. After dissolution by stirring, a portion of the solvent was removed by evaporation slowly and the solution was filtered to obtain a solid. Subsequently, the resultant solid was dried at room temperature under vacuum to obtain the crystal form K of ginsenoside C-K.

Example 17

Figure 14:
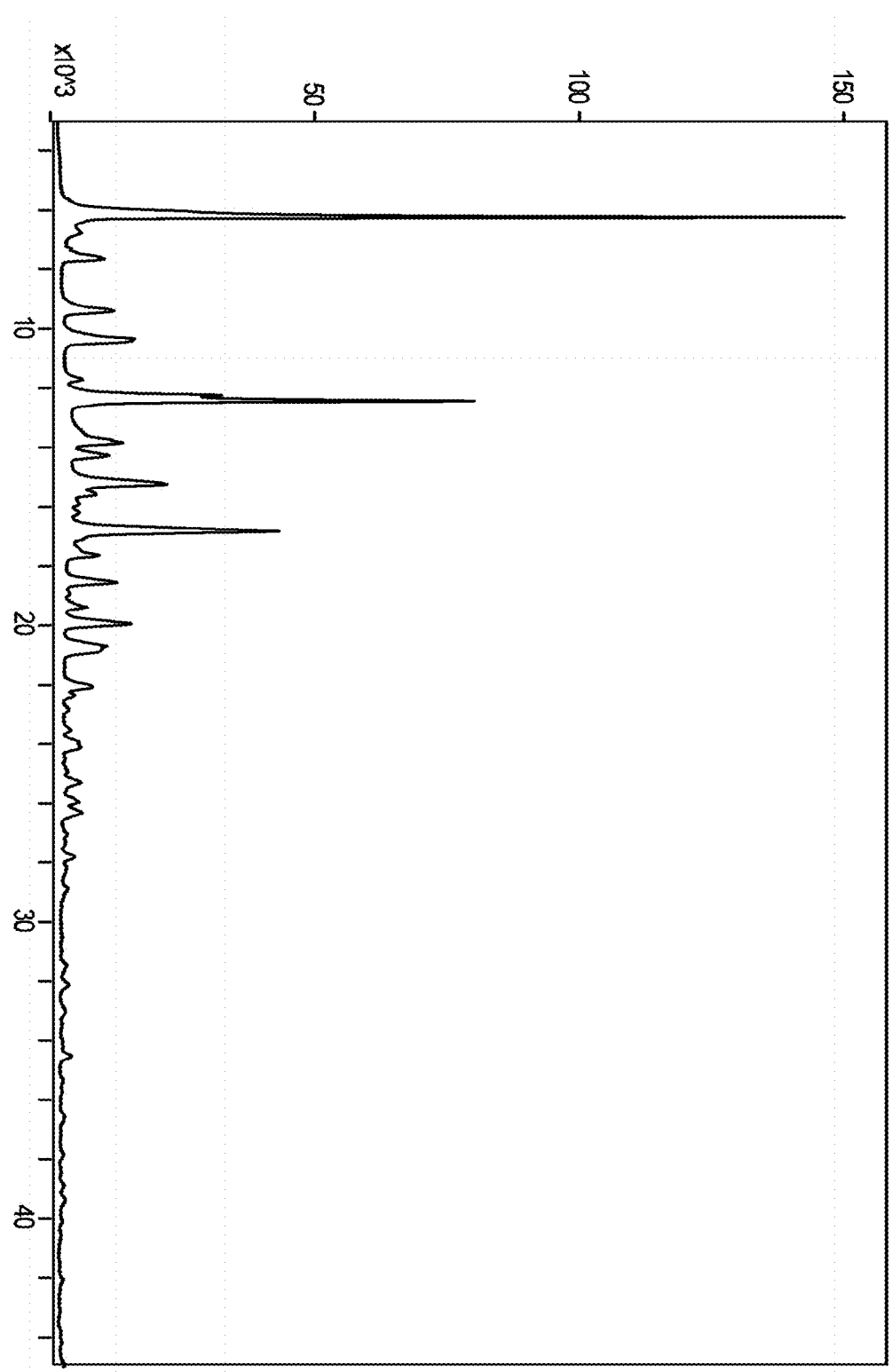
FIG. 14 is an X-ray powder diffraction pattern of the crystal form K obtained in Example 16.
Figure 15:
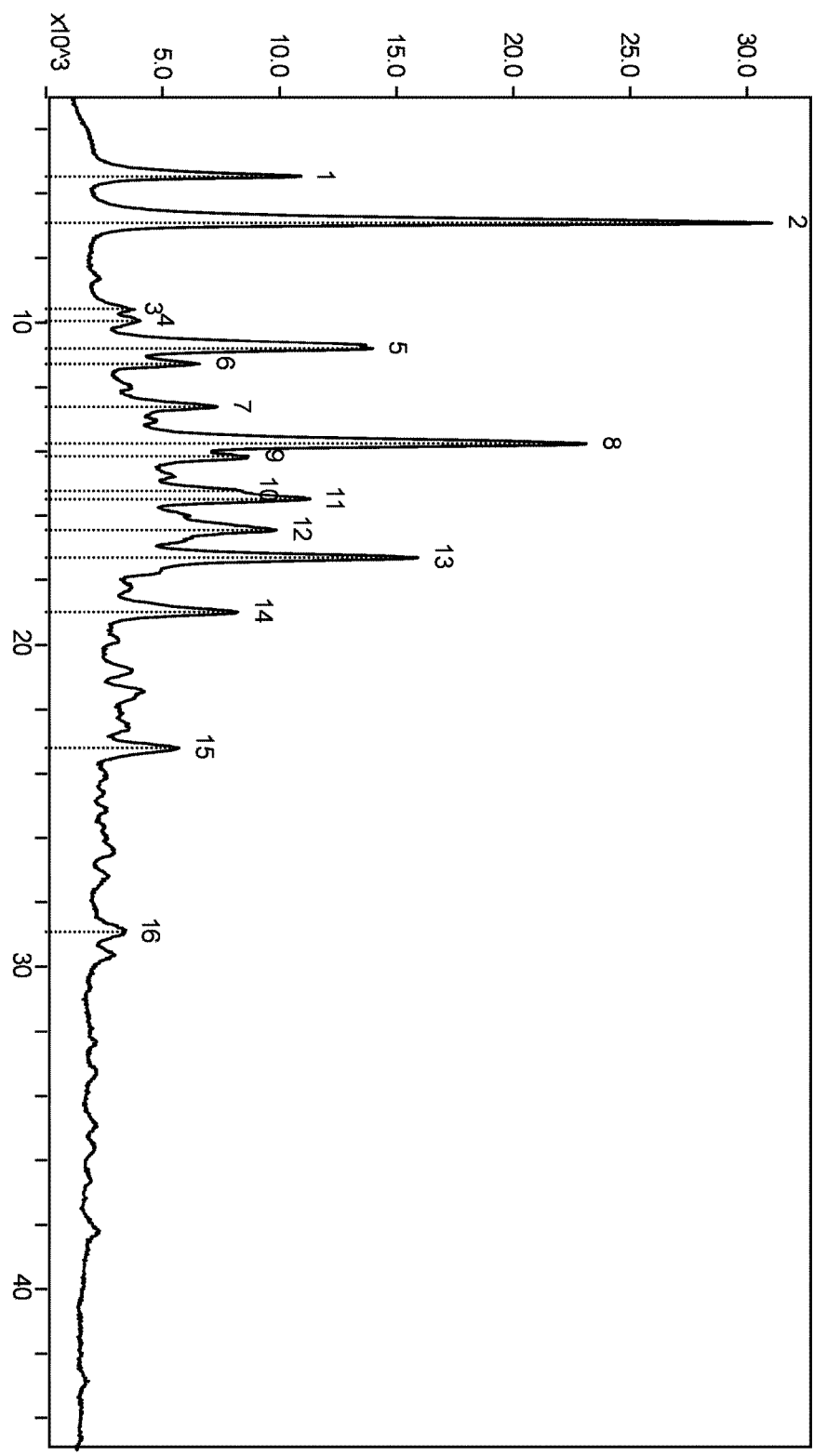
FIG. 15 is an X-ray powder diffraction pattern of the crystal form L of ginsenoside C-K.
Figure 16:
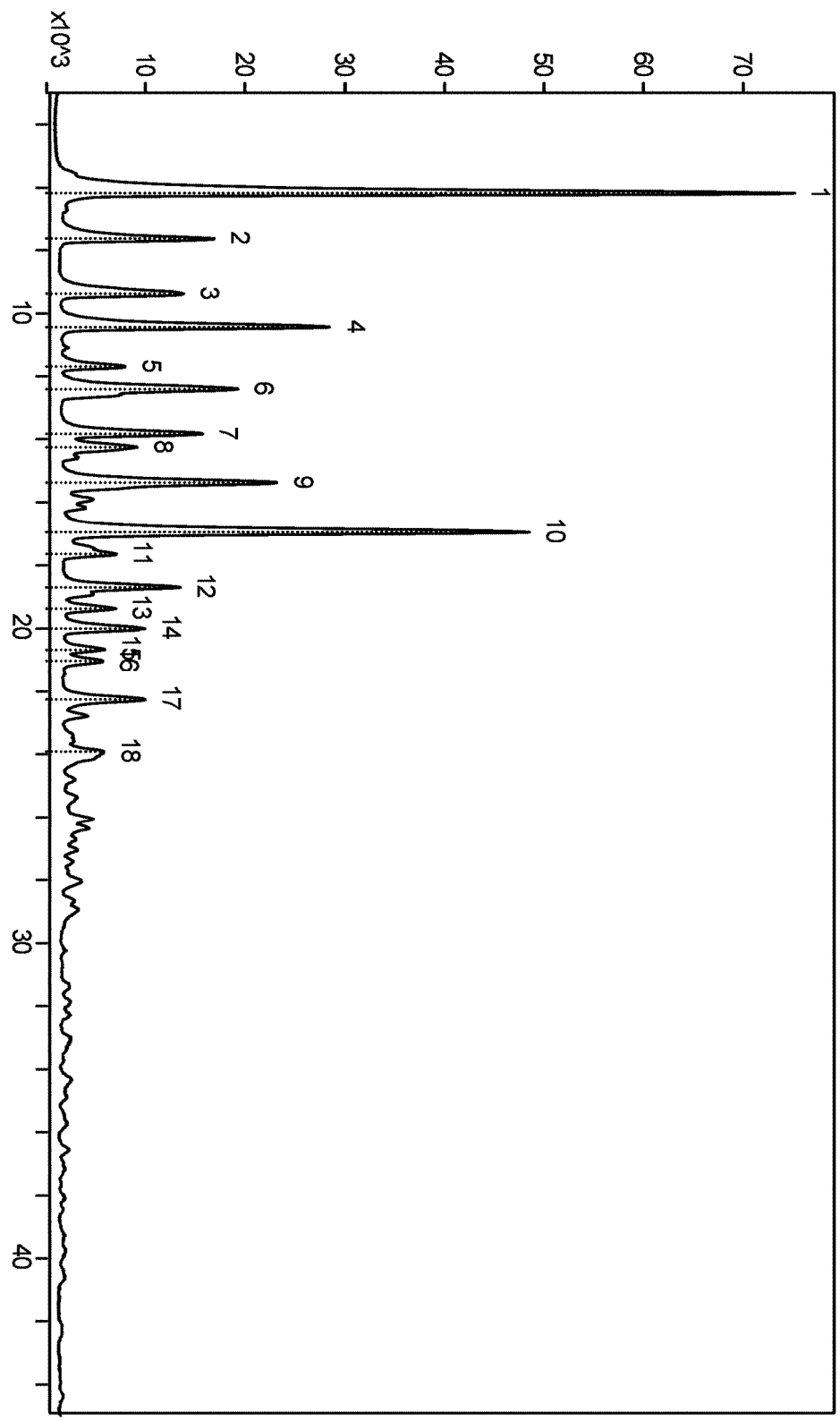
FIG. 16 is an X-ray powder diffraction pattern of the crystal form M of ginsenoside C-K.
Figure 17:
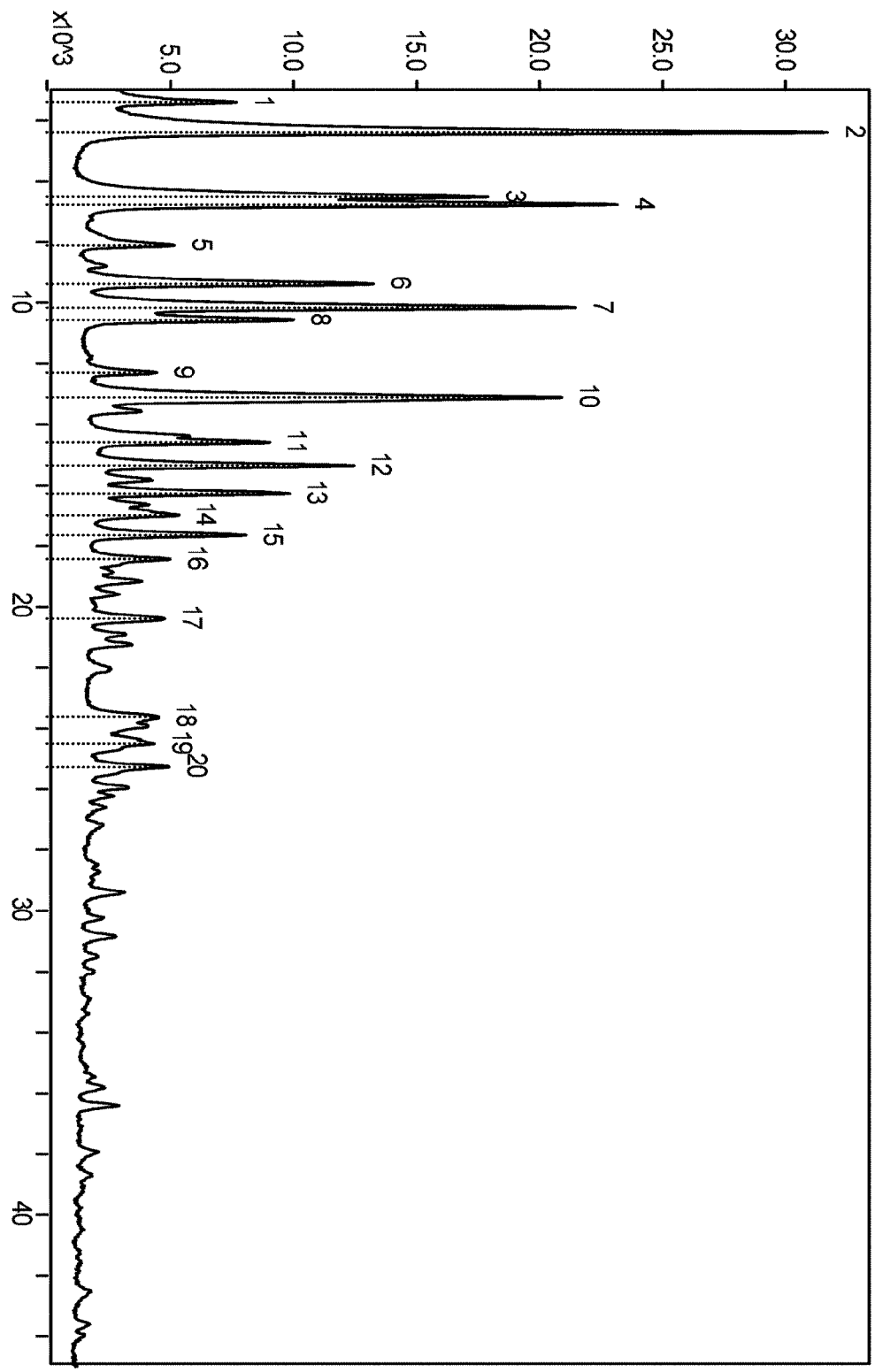
FIG. 17 is an X-ray powder diffraction pattern of the crystal form N of ginsenoside C-K.
Figure 18:
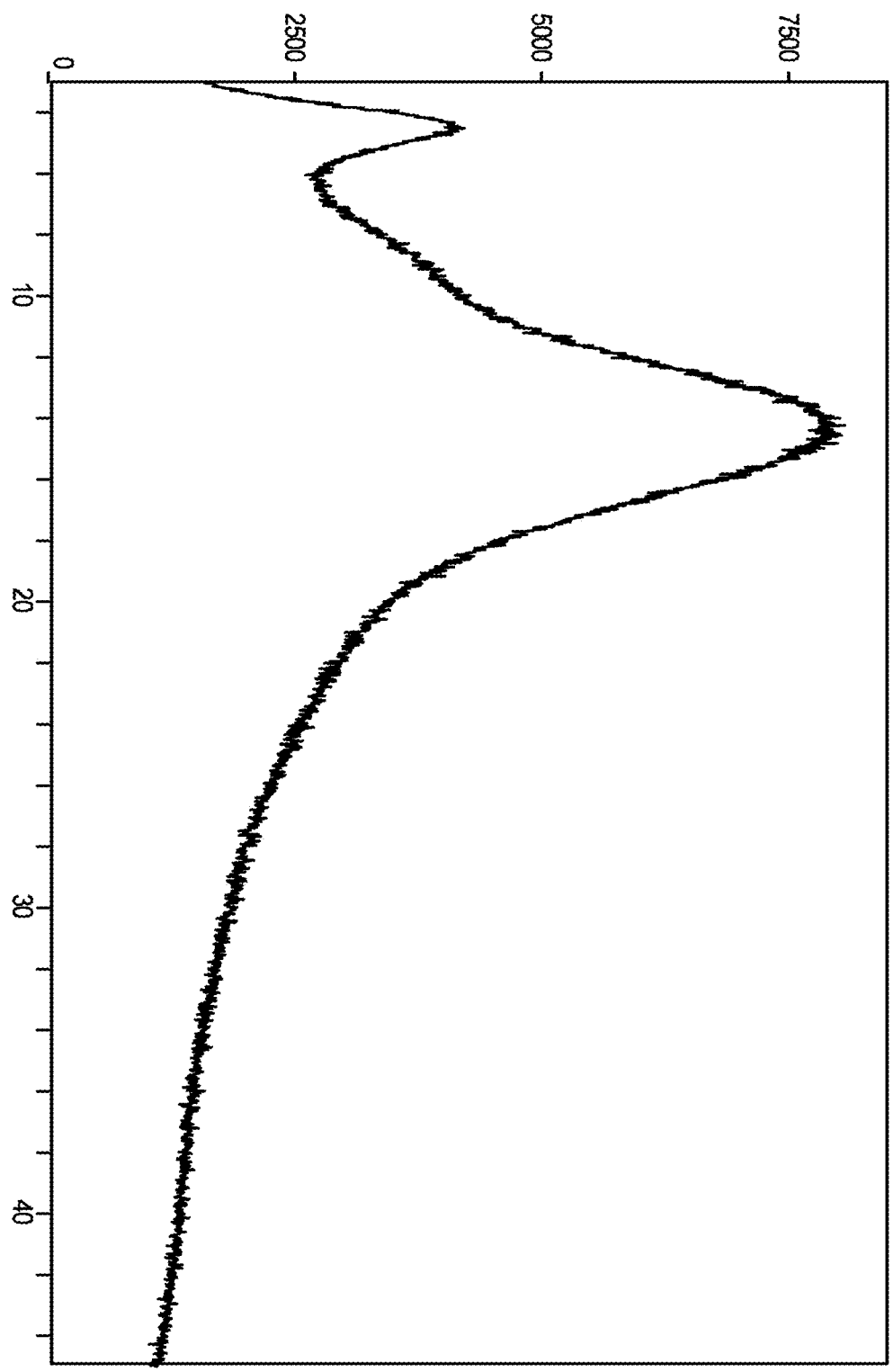
FIG. 18 is an X-ray powder diffraction pattern of the crystal form O of ginsenoside C-K.

4 g ginsenoside C-K was placed in a container, into which 20 ml isopropanol (analytical grade) and 20 ml water were added, and the temperature was increased to 70° C. After dissolution by stirring, another 40 ml water was added slowly, and it was filtered to obtain a solid. Subsequently, the resultant solid was dried at room temperature under vacuum to obtain the crystal form K of ginsenoside C-K. Its XRPD pattern was shown in FIG. 14.

8. Preparation of the Crystal Form L of Ginsenoside C-K

Example 18

8 g ginsenoside C-K was placed in a container, into which 120 ml methanol was added and the temperature was increased to 40° C. After dissolution by stirring, the solution was cooled down to 25° C., and it was still clear. Subsequently, 80 ml water was added dropwise at a rate of 1 ml/min. It was then filtered, and the filter cake was dried at 40° C. in a vacuum drying oven to obtain the crystal form L of ginsenoside C-K.

9. Preparation of the Crystal Form N of Ginsenoside C-K

Example 19

2 g ginsenoside C-K was placed in a container, into which 20 ml water and 100 ml acetonitrile were added, and the temperature was increased to 45° C. After dissolution by stirring, it was cooled down to 4° C., and the solution was still clear. 120 ml water was slowly added dropwise, and it was filtered to obtain the solid. Subsequently, the resultant solid was dried under vacuum to obtain the crystal form N of ginsenoside C-K.

Example 20

3 g ginsenoside C-K was placed in a container, into which 20 ml water and 100 ml acetonitrile were added, and the temperature was increased to 50° C. After dissolution by stirring, it was cooled down to 20° C., and the solution was still clear. 200 ml water was slowly added dropwise, and it was filtered to obtain the solid. Subsequently, the resultant solid was dried under vacuum to obtain the crystal form N of ginsenoside C-K.

Example 21

2.5 g ginsenoside C-K was placed in a container, into which 20 ml water and 100 ml acetonitrile were added, and the temperature was increased to 50° C. After dissolution by stirring, it was cooled down to 12° C., and the solution was still clear. 150 ml water was slowly added dropwise, and it was filtered to obtain a solid. Subsequently, the resultant solid was dried under vacuum to obtain the crystal form N of ginsenoside C-K.

10. Preparation of the Crystal Form O of Ginsenoside C-K

Example 22

6 g ginsenoside C-K was added to 50 ml ethanol, and the temperature was increased to 50° C. After dissolution, the solvent was removed by rotary evaporation at 50° C. to obtain the solid, which was then dried under vacuum to obtain the crystal form O of ginsenoside C-K.

Example 23

0.7 g ginsenoside C-K was added to 15 ml ethyl acetate and 45 ml acetone, and the temperature was increased to 50° C. After dissolution, the solvent was removed by rotary evaporation at 50° C. to obtain the solid, which was then dried under vacuum to obtain the crystal form O of ginsenoside C-K.

Example 24

6 g ginsenoside C-K was added to 20 ml DMF. After dissolution by stirring, 40 ml water was added. It was then stirred for 10 min and filtered. The resultant solid was dried under vacuum to obtain the crystal form O of ginsenoside C-K.

11. Preparation of the Crystal Form M of Ginsenoside C-K

Example 25

1 g the crystal form O of ginsenoside C-K was added to 20 ml ethanol and 80 ml benzene. After dissolution by stirring, the solvent was removed by evaporation slowly. It was then filtered, and the resultant solid was dried under vacuum to obtain the crystal form M of ginsenoside C-K.

The invention claimed is:

1. A crystal form A of ginsenoside C-K, characterized by an XRPD pattern comprising peaks at 2θ values of 5.44, 7.06, 8.94, 11.61, 13.70, 14.43, 15.81, 17.22, 17.84, 18.71, and 19.01 degrees, wherein the error range of the 2θ values is ±0.2 degrees.

2. The crystal form A according to claim 1, wherein the XRPD pattern further comprises peaks at 2θ values of 9.51, 12.28, 16.14, 20.90, 21.90, 25.68, and 27.71 degrees, wherein the error range of the 2θ values is ±0.2 degrees.

3. A method for preparing the crystal form A of ginsenoside C-K according to claim 1, comprising:
   (1) dissolving ginsenoside C-K in 1-methyl-2-pyrrolidone or a mixed solvent consisting of 1-methyl-2-pyrrolidone and acetone;
   (2) removing the solvent slowly by evaporation; and
   (3) drying the resultant solid under vacuum to obtain the crystal form A of ginsenoside C-K.

4. The crystal form A according to claim 1, wherein the XRPD pattern is substantially the same as FIG. 1.

5. The crystal form A according to claim 1, further characterized by a DSC pattern comprising an endothermic peak at 117±5° C.

6. The crystal form A according to claim 2, further characterized by a DSC pattern comprising an endothermic peak at 117±5° C.

7. The crystal form A according to claim 4, further characterized by a DSC pattern comprising an endothermic peak at 117±5° C.

8. A method for preparing the crystal form A of ginsenoside C-K according to claim 1, comprising:
   (1) dissolving ginsenoside C-K in 1-methyl-2-pyrrolidone;
   (2) adding an anti-solvent dropwise, wherein the anti-solvent is selected from the group consisting of isopropyl ether, water, and nitromethane; and
   (3) after stirring for a while, filtering the resultant suspension, and drying the filter cake under vacuum to obtain the crystal form A of ginsenoside C-K.

* * * * *